United States Patent
Henry et al.

[11] Patent Number: 6,113,763
[45] Date of Patent: Sep. 5, 2000

[54] METHOD FOR MEASURING CELLULAR CHEMICAL PROFILES

[75] Inventors: Douglas N. Henry; Patrick F. Dillon, both of East Lansing, Mich.

[73] Assignee: Board of Trustee operating Michigan State University, East Lansing, Mich.

[21] Appl. No.: 08/959,686

[22] Filed: Oct. 29, 1997

Related U.S. Application Data

[60] Provisional application No. 60/029,914, Nov. 4, 1996.

[51] Int. Cl.[7] .................................................. G01N 27/26
[52] U.S. Cl. .......................................................... 204/451
[58] Field of Search ................................... 204/450, 451, 204/456

[56] References Cited

U.S. PATENT DOCUMENTS

| | | |
|---|---|---|
| 5,213,669 | 5/1993 | Guttman . |
| 5,370,777 | 12/1994 | Guttman et al. . |
| 5,431,793 | 7/1995 | Wang et al. . |
| 5,490,909 | 2/1996 | Wang et al. . |
| 5,637,471 | 6/1997 | Artavanis-Tsakonas et al. ..... 435/7.23 |

FOREIGN PATENT DOCUMENTS

Wo/9315395  8/1993  WIPO .

OTHER PUBLICATIONS

Egil Jellum ("Capillary electrophoresis for medical diagnosis", J. Capillary Electrophor. (1994), 1(2), 97–105). Month unknown.

Kennedy et al. ("Microcolumn Separations and the Analysis of Single Cells", Science, 246, 57–63), 1989. Month unknown.

Sloss et al., ("Capillary Electrophoresis for the Analysis of Single Cells", Handb. Capillary Electrophor. (1994), 391–417. Ed. Landers, CRC, Boca Raton, Fla.). Month unknown.

Giometti et al. ("Analysis of proteins from human breast epithelial cells using two–dimensional gel eletrophoresis", Electrophoresis 1995, 16, 1215–1224). Month unknown.

Jellum et al. ("Capillary electrophoresis for diagnosis and studies of human disease, particularly metabolic disorders", J. Chromatog., 559 (1991) 455–465). Month unknown .

Vinores et al. ("Aldose Reductase Expression in Human Diabetic Retina and Retinal Pigment Epithelium", Diabetes, 37, 1658–1664), 1988. Month unknown.

Jellum, E., et al., J. of Chromatography 559:455–465 (1991). Month unknown.

The DCCT Research Group. N. Engl J. Med (Sep. 30) 329 (14):977–986 (1993). Month unknown.

Heilig, C.W., et al., J. Clin Invest. 96:1802–1814 (1995). Month unknown.

Tilton, R.G., et al., Kidney International 41:778–788 (1992). Month unknown.

Wolf, B.A. et al., J. Clin Invest 87:31–38 1991. Month unknown.

Stevens, J.J., Diabetic Medicine 12:292–295 (1995). Month unknown.

Lee, et al., Anal. chem 64, 3045–3051 (1992). Month unknown.

MacGregor, L.C., et al., J. Biol Chem 261:4046–4055 (1986). Month unknown.

(List continued on next page.)

*Primary Examiner*—Jill Warden
*Assistant Examiner*—Alex Noguerola
*Attorney, Agent, or Firm*—Ian C. McLeod

[57] ABSTRACT

A method for spectrographically providing a chemical profile of mammalian cells in vitro using capillary (10) electrophoresis is described. The method enables rapid determination of the chemicals, especially human cell metabolites, in the case of diabetes. The method is rapid, efficient and reproducible and enables the diagnosis of the progress of a disease at the cellular level.

29 Claims, 21 Drawing Sheets

OTHER PUBLICATIONS

Vinores, S.A., et al., Diabetes 37:1658–1664 (1988). Month unknown.

Kushmerick, M.J., et al., J. Biol. Chem 261:14420–14429 (1986). Month unknown.

Xia, P., et al., J. Clin Invest. 96:733–740 Aug. (1995).

Xue, Q., et al., Journal of Chromatography A, 661:287–295 (1994).

Brands, M.W., et al., Hypertension vol. 27, No. 3 Part 2 pp. 735–739 (Mar. 1996).

Nava, E., et al., J. of Hypertension 13 (suppl 2) S39–S48 (1995). Month unknown.

Porte Jr., D. et al., Science 272:699–700 (May 1996).

Ishii, H., et al., Science 272:728–731 (May 1996).

Burg, M.B., et al., The Journal of Clinical Investigation, Inc. 81:635–640 (1988) Mar.

Dolnik, V. et al., Journal of Chromatography A, 716:269–277 (1995). Month unknown.

Heileg, C.W., et al., Kidney International 52 (Suppl. 60): S–91–S–99 (1997). Month unknown.

Kamaryt, J., et al., Eur J. Clin Chem Clin Biochem. 34:969–973 (1996). Month unknown.

King, G.L., et al., Diabetes 45 (suppl 3):S105–S108 (Jul. 1996).

Lindsay, R.M., et al., British Journal of Pharmacology 120:1–6 (1997). Month unknown.

Nakamura, J., et al., Am. J. Physiol 262 (Endocrinol. Metab 25):E417–E426 (1992).

Nava, E., et al., Changes In Nitric Oxide Release in vivo Response to Vasoactive Substances pp. 1211–1216 (Aug. 1996).

Ng, M. and Blaschke T.F., Anal. Chem. 64, 1682–1684 (1992).

Nishimura, C., et al., Diabetologia 37:328–330 (1994).

Shao, X., et al., Journal of Chromatography A, 680:463–468 (1994).

Simon, P., et al., Journal of Chromatography B, 679:103–112 (1996).

Smits, P., et al., Diabetes 42:148–153 (1993).

Stevens, M.J., et al., Am. J. Physiol 265 (Endocrinol, Metab 28):E428–E438 (1993).

Tseng, H.C., et al. Analytical Biochemistry 222:55–58 (1994).

VandenEnden, M.K. et al., Investigative Opthalmology & Visual Science 36 (No. 8):1675–1685 (1995).

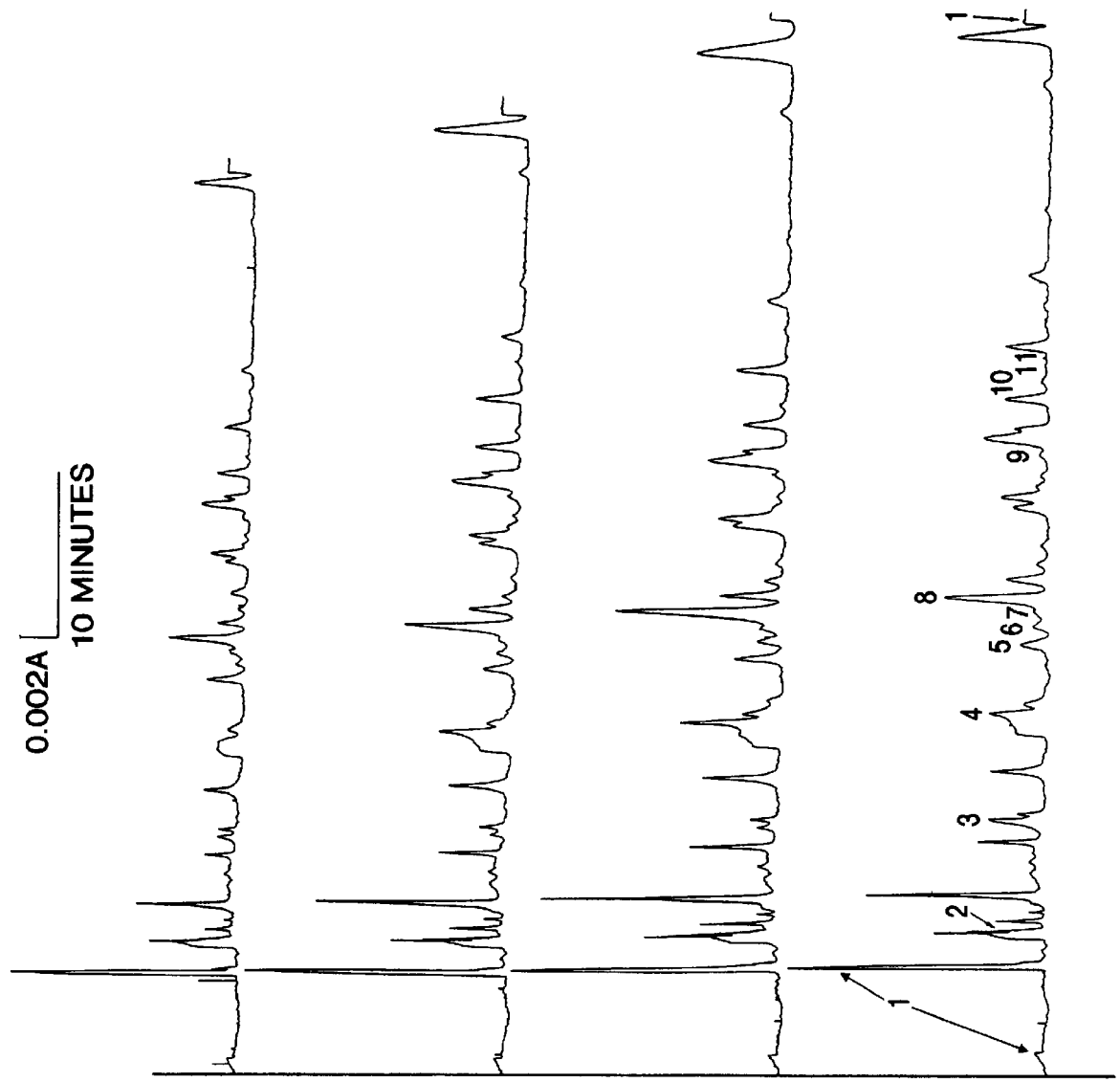

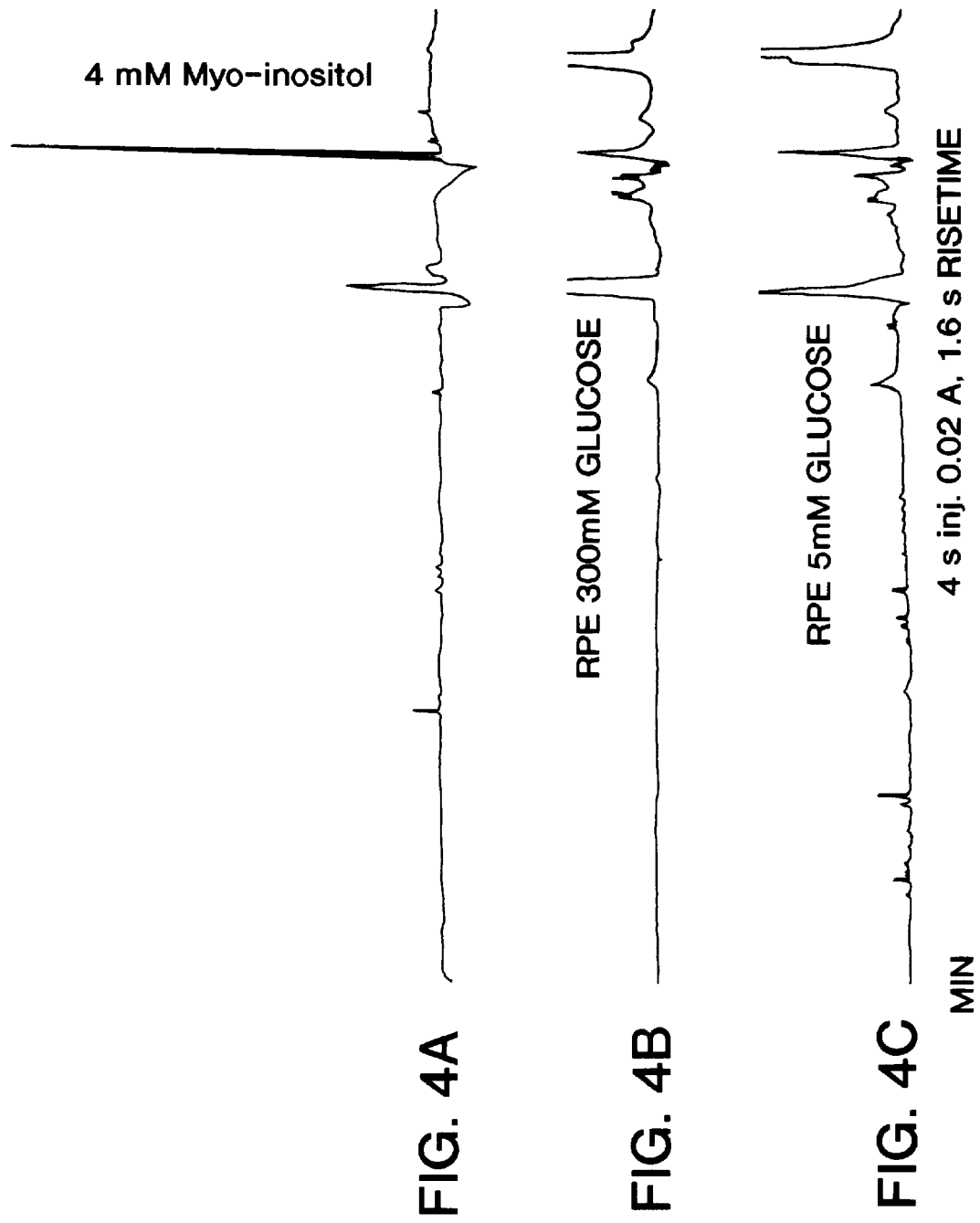

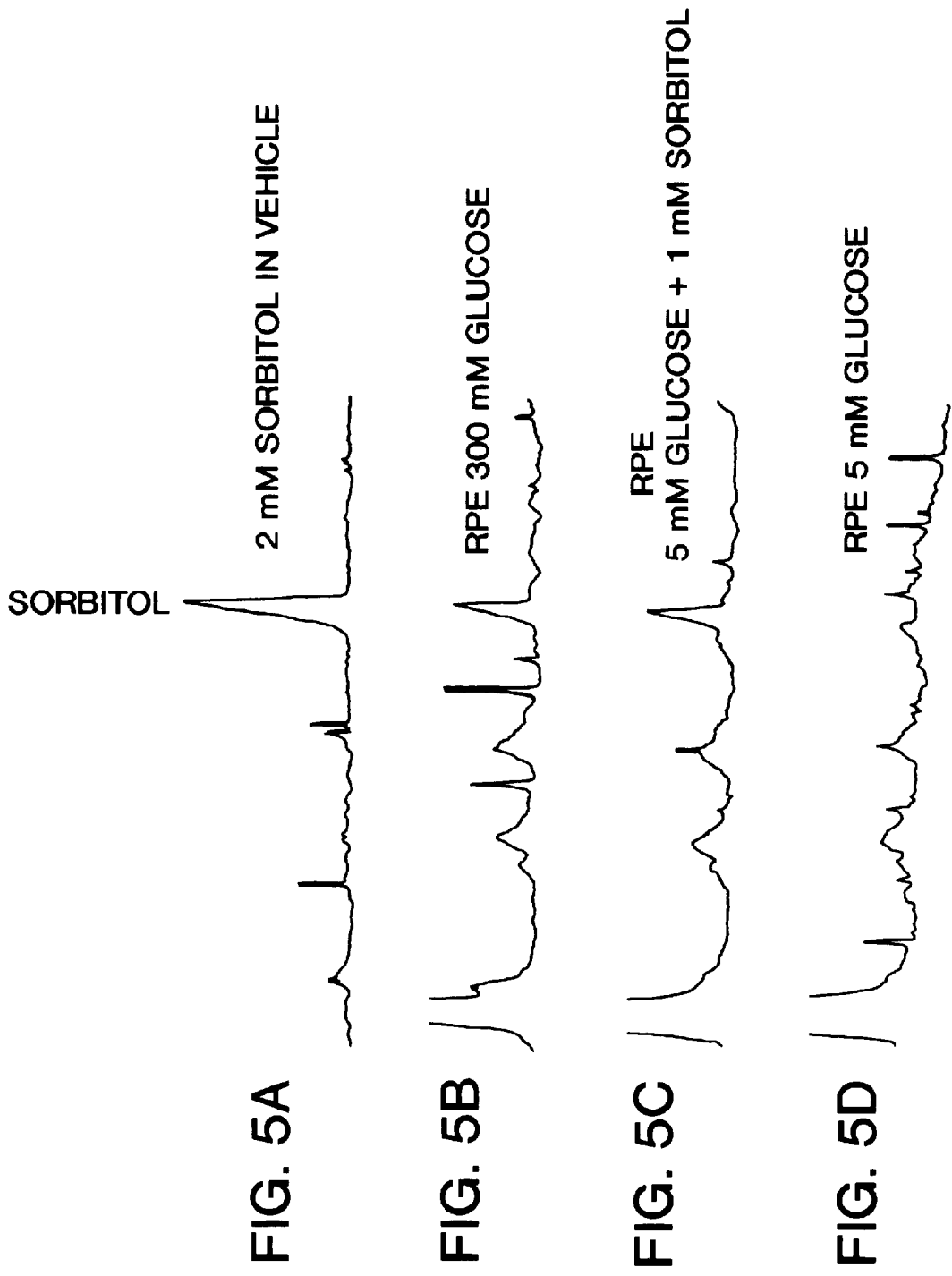

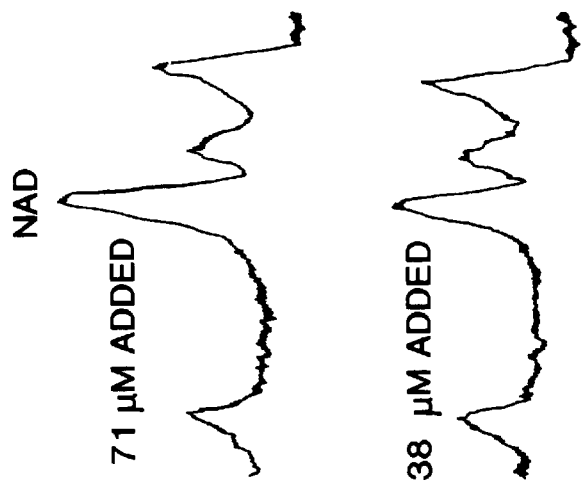
FIG. 7A — NAD 71 µM ADDED
FIG. 7B — 38 µM ADDED
FIG. 7C — RPE 300 mM GLUCOSE
8 s inj., 0.02 A, 0.8 s RISETIME
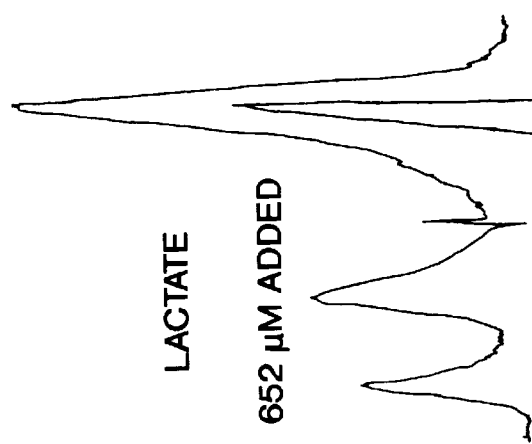
FIG. 6A — LACTATE 652 µM ADDED
FIG. 6B — RPE 5 mM GLUCOSE
8 s inj., 0.02 A, 0.8 s RISETIME

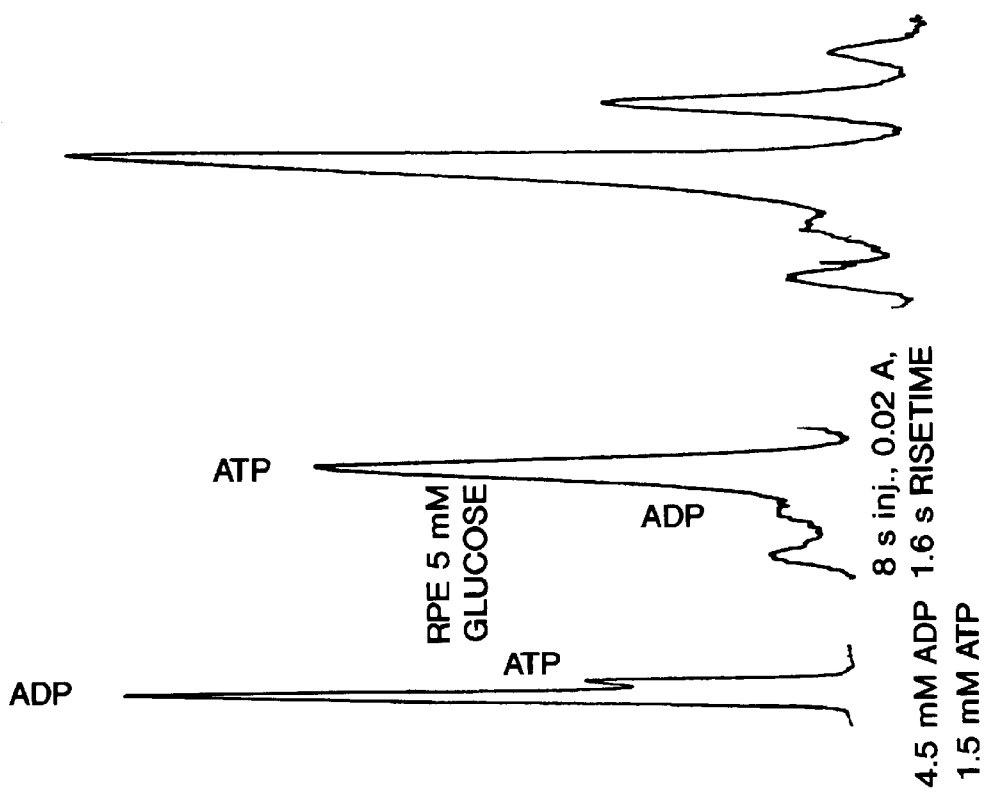
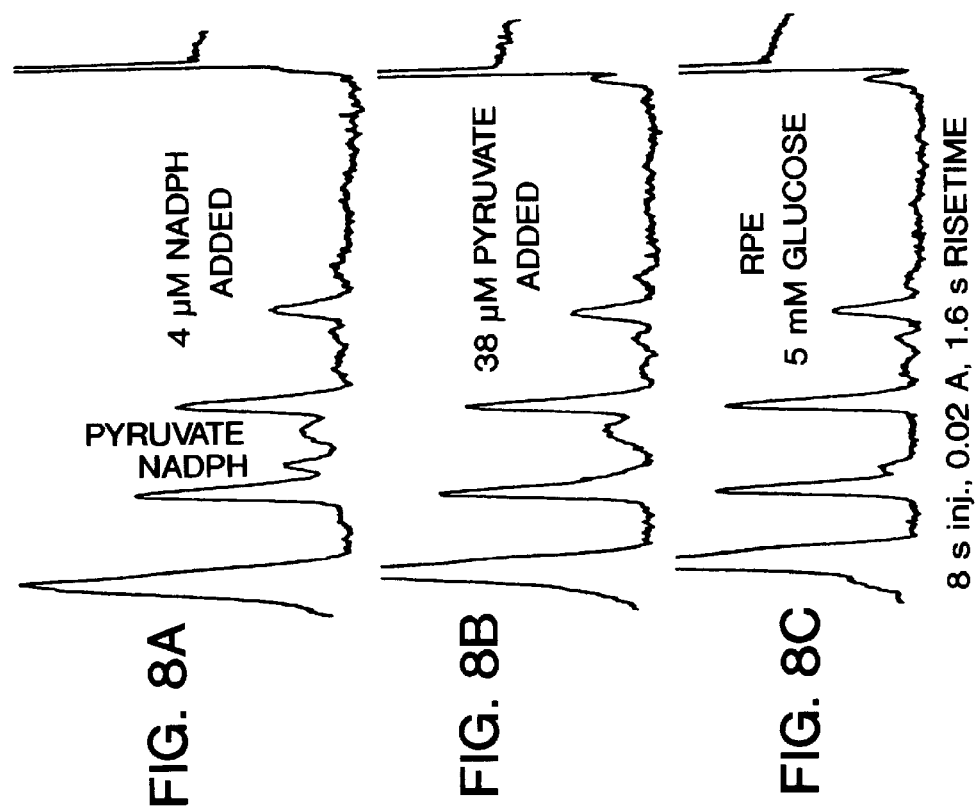

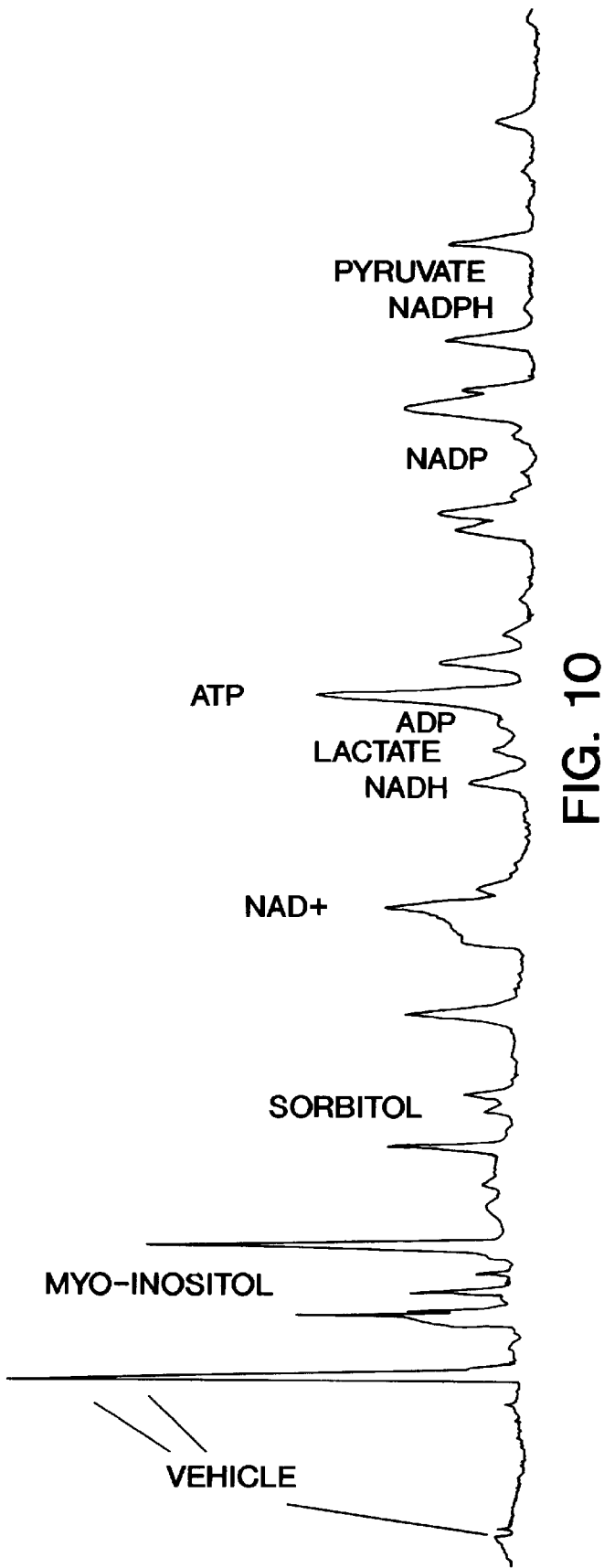

METHOD FOR MEASURING CELLULAR CHEMICAL PROFILES

This application claims the benefit of U.S. Provisional Application(s) No(s).: 60/029,914 filed Nov. 4, 1996.

GOVERNMENT RIGHTS

This invention was funded by NICHD 1992-1995 Center Grant 1 P30 HD 28820; and NIDDK-NIH Physician Scientist Award 1K11DK02193-01 and U.S. Public Health Science Grant No. 42268. The U.S. Government has certain rights in this invention.

BACKGROUND OF THE INVENTION (1) Summary of the Invention

The present invention relates to a method for quantitatively chemically profiling mammalian cells involved in a disease using capillary electrophoresis. The present invention is particularly effective in testing for metabolites of cells in diabetes. The method can be used to test the effectiveness of aldose reductase inhibitors.

(2) Description of Related Art

Capillary electrophoresis is well known to those skilled in the art. Illustrative are U.S. Pat. No. 5,213,669 to Guttman; U.S. Pat. No. 5,370,777 to Guttman et al; U.S. Pat. No. 5,431,793 to Wang et al; U.S. Pat. No. 5,490,909 to Wang et al; PCT 93/15395 and Jellum, E., et al., J. of Chromatography 559:455–465 (1991). The method has been used with proteins, amino acids and nucleotides.

Presently, great interest exists in the changes of metabolites in cells exposed to elevations in glucose as in diabetes. These models include: tissue culture models of diabetes, transgenic diabetic models, animal models of diabetes, human models including clinical intervention trials to ameliorate the effects of diabetes on tissues (nerve, kidney, retinal and blood vessels) involved in the long-term complications from the disease. In order to study changes of intracellular metabolites in diabetes, investigators have had to use high performance liquid chromatography (HPLC) or bioassays. These assays are laborious, expensive, time consuming, often frustrated by technical problems and require large amounts of tissue to examine. Also, HPLC or bioassays require hours to days to run and standardize data. By example, Phase III clinical trials on the efficacy of aldose reductase inhibitors in the treatment and/or prevention of long-term complications (neuropathy) from diabetes are presently underway. These human trials require the quantitation of sorbitol and myo-inositol from peripheral nerve biopsy (such as the sural nerve). The specimen of nerve tissue must undergo derivitization and extraction of carbohydrates for the determination of tissue sorbitol and myo-inositol levels by HPLC which necessitates the use of almost one cm of nerve biopsy. There is a need for a faster and better method for analyzing for changes in the metabolites.

While the findings of the Diabetes Control and Complications Trial have incontrovertibly removed any doubt regarding the role of elevated blood glucose and the risk for long-term complications from diabetes, the mechanism(s) of tissue injury in diabetes are poorly understood (The DCCT Research Group. N. Engl J Med (September 30) 329 (14) :977–986 (1993)). Interrelated metabolic imbalances linked to diabetes and glucose induced cellular dysfunction have been proposed as putative pathogenic mechanisms resulting in the vascular, renal, retinal and nerve complications of diabetes. These interrelated metabolic pathways (FIG. 1) include increased flux or transport of glucose into the cell (Henry, D. N., et al., J. Am Society of Nephr. (7)9:1871 (1996): and Heilig, C. W., et al., J. Clin. Invest. 96:1802–1814 (1995)), polyol metabolism with the accumulation of sorbitol and change in myo-inositol (MI) concentration (Gabbay, K. H., Annu Rev Med:26:521–536 (1975); and Winegrad, A. I., et al., N Engl J Med 16:295 (25):1416–1421 (Dec. 16, 1976)), altered cellular redox potential (Tilton, R. G., et al., Kidney International 41:778–788 (1992); and Williamson, J. R., et al., Diabetes 42:801–813 (1993)), de novo formation of diacylglycerol (DAG) leading to activation of protein kinases (PKC) (Wolf, B. A., et al., J Clin Invest 87:31–38 (1990)), decreased nitric oxide (endothelial derived relaxation factor) formation (Greene, D. A., et al., Diabetes and Metabolism Reviews 9(3):189–217 (1993); and Stevens, J. J., Diabetic Medicine 12:292–295 (1995)), and non-enzymatic glycosylation of proteins (Brownlee, M., et al., Ann Intern Med Oct; 101(4) :527–537 (1984)). Presently, there are no means to concomitantly measure the metabolic intermediates and/or endproducts of these pathways as they change in diabetes.

CE has been applied to the diagnosis and studies of human disease, particularly metabolic disorders such as homocytinuia, cystinuria, glutationone synthetase and adenylsuccinases deficiencies in urine and blood (Jellum, E., et al., J. Chromatography 559:455–465 (1991)). CE has also been successfully employed to measure nitrite and nitrates in plasma as indirect measures of nitric oxide in human subjects (Leone, A. M., et al., Biochem Biophy Res Comm 200(2):951–957 (1994); and Ueda, T., et al., Electrophoresis 16:1002–1004 (1995)). CE has been used to test for glycosolated hemoglobin determination in diabetes (Doelman, C. J., et al., Clin Chem Apr 43(4):644–648 (1997); and Lillard, S. J., et al., J Chromatogr B Biomed Appl Dec 13; 687(2) :363–369 (1996)). The analysis of single cells for protein is described by Lee et al, Anal. Chem 64, 3045–3051 (1992). What is needed is a method which provides a complete profile of the components of multiple cells from the same sample. This provides a basis for determining whether or not the cells are diseased.

OBJECTS

It is an object of the present invention to chemically profile mammalian cells in vitro in the presence of or absence of compounds which affect the profile using capillary electrophoresis. In particular, it is an object of the present invention to provide an in vitro method which uses capillary electrophoresis to measure intracellular metabolites, proteins and signal transduction molecules from tissues and cultures exposed to disease conditions on cellular metabolism in vitro and in vivo. Further, it is an object of the present invention to provide a method which is much simpler and more economical than high pressure chromatography (HPLC). These and other objects of the present invention will become increasingly apparent by reference to the following description and the drawings.

BRIEF DESCRIPTION OF DRAWINGS

FIGS. 3A to 3D are graphs showing electropherograms of RPE cells grown in 5 mM (FIG. 3B), 20 mM (FIG. 3C), or 300 mM (FIG. 3A) glucose for 4 days. The heights of each peak reflect the amount of each metabolite when corrected for protein content (50% reduction in protein content when grown in 300 mM glucose). 5 mM glucose sample+2.5 mM sorbitol added to extract (FIG. 3D).

FIGS. 4A, 4B and 4C are graphs showing identification of myo-Inositol by Electrophoretic Migration by CE. 4 mM myo-inositol was added to the carrier buffer (FIG. 4A) and myo-inositol peak was compared to RPE cell samples grown in 5 mM (FIG. 4C) and 300 mM glucose (FIG. 4B).

FIGS. 5A, 5B, 5C and 5D are graphs showing identification of Sorbitol Electrophoretic Migration by CE. 2 mM sorbitol was added to carrier buffer (vehicle) and to sample from RPE cells grown in 5 mM glucose. Electrophoretic migration peaks were compared between spiked vehicle (FIG. 5A) and RPE samples from 5 mM (FIG. 5D), 5 mM+1 mM sorbitol added (FIG. 5C), and 300 mM (FIG. 5B) glucose.

FIGS. 6A and 6B are graphs showing identification of lactate Electrophoretic Migration by CE. 65.2 $\mu$M lactate was added (FIG. 6A) to neutralized sample from RPE cells grown in 5 mM glucose (FIG. 6B) and electrophoretic migration compared to unspiked RPE sample.

FIGS. 7A, 7B and 7C are graphs showing identification of NAD Electrophoretic Migration by CE. 71 $\mu$M (FIG. 7A) and 38 $\mu$M (FIG. 7B) NAD was added to sample from RPE cells grown in 300 mM glucose (FIG. 7C). Electrophoretic migration was compared between spiked and unspiked RPE samples.

FIGS. 8A, 8B and 8C are graphs showing identification of NADPH and Pyruvate Electrophoretic Migration by CE. 4 $\mu$M (FIG. 8A) and 38 $\mu$M pyruvate (FIG. 8B) was added to neutralized sample from RPE cells grown in 5 mM glucose (FIG. 8C). Electrophoretic migration was compared between spiked and unspiked RPE samples.

FIGS. 9A, 9B and 9C are graphs showing identification of ADP and ATP Electrophoretic Migration by CE. 4.5 mM ADP (FIG. 9A) and 1.5 mM ATP was added to the carrier extract. 39 $\mu$M ATP was added to the neutralized sample from RPE cells grown in 20 mM glucose (FIG. 9B and 9C). Electrophoretic migration was compared between spiked and unspiked RPE samples.

FIGS. 10 to 15 are graphs showing spectrographic analysis of products produced by capillary electrophoresis.

FIG. 10 is with 5 mM glucose and without sorbitol.

FIG. 11 is with glucose and with sorbitol.

FIG. 12 is with 300 mM glucose.

FIGS. 13 to 15 are controls with the vehicle alone (FIG. 15) and with sorbitol (FIG. 13) and myo-inositol (FIG. 14).

DESCRIPTION OF PREFERRED EMBODIMENTS

Figure 1:
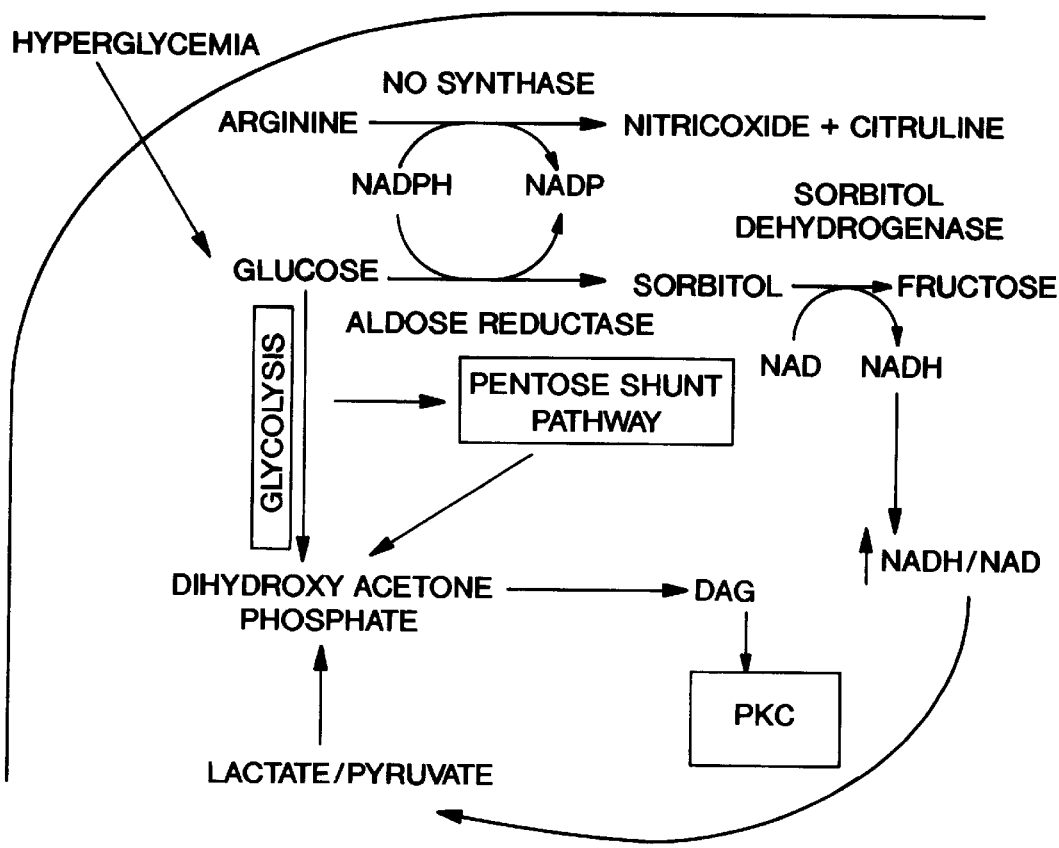
FIG. 1 is a chart showing inter-related metabolic pathways believed to contribute to the development of long-term complications of diabetes.

The present invention relates to an in vitro method for chemically profiling mammalian cells involved in a disease by measuring chemicals in the cells which comprises: isolating mammalian cells; disrupting the cells in a fluid medium so that cellular debris as a solvent phase and a liquid phase with multiple of the chemicals in admixture; removing the debris from the liquid phase; subjecting the liquid phase to capillary electrophoresis in a single run wherein the chemicals are separated in the liquid phase; continuously scanning the chemicals produced by the capillary electrophoresis with a spectrophotometer which measures light absorbance to produce a chart with peaks of light absorbance for each of the chemicals; and determining the chemical profile of the cells from the peaks.

Further, the present invention relates to an in vitro method for chemically profiling mammalian cells involved in diabetes by measuring chemicals produced by the cells which comprises: isolating mammalian cells; disrupting the cells in a fluid medium so that cellular debris in a solid phase and a liquid phase with multiple of the chemicals in admixture; removing the debris from the liquid phase; subjecting the liquid phase to capillary electrophoresis in a single run wherein the chemicals are separated in the liquid phase; continuously scanning the metabolites produced by the capillary electrophoresis with a spectrophotometer which measures light absorbance to produce a chart with peaks of light absorbance for each of the chemicals; and calculating an area of at least some of the peaks to determine a quantity selected of the chemicals in the cells.

The present invention relates to a method for quantitatively testing a chemical compound in vitro for effectiveness in altering enzyme activity of at least one enzyme in a mammalian cell involved in a disease by measuring enzymatic products which comprises: treating mammalian cells in a culture medium in vitro with the chemical compound to be tested; separating the treated cells from the culture medium; disrupting the cells in a fluid medium so that cellular debris as a solid phase and a liquid phase with multiple products of the enzyme are produced in admixture; removing the debris from the liquid phase; subjecting the liquid phase to capillary electrophoresis in a single run wherein the products produced by the enzyme with the compound are separated in the liquid phase; continuously scanning the enzymatic products produced by the capillary electrophoresis with a spectrophotometer which measures light absorbance to produce a chart with peaks of light absorbance for each of the products; and determining the effectiveness of the compound in altering the enzyme activity from the peaks as compared to a control without the compound.

Further, the present invention relates to a method for quantitatively testing a chemical compound in vitro for effectiveness in altering enzyme activity at least one enzyme involved in diabetes by measuring enzymatic products which comprises: treating mammalian cells in a culture medium in vitro with the chemical compound to be tested; separating the treated cells from the culture medium; disrupting the cells in a fluid medium so that cellular debris as a solid phase and a liquid phase with multiple products of the enzyme are produced in admixture; removing the debris from the liquid phase; subjecting the liquid phase to capillary electrophoresis in a single run wherein the products produced by the enzyme with the compound are separated in the liquid phase; continuously scanning the products produced by the capillary electrophoresis with a spectrophotometer which measures light absorbance to produce a chart with peaks of light absorbance for each of the products; calculating areas of the peaks to determine a quantity of each of the products; and determining the effectiveness of the compound in altering the enzyme activity from the peaks as compared to a control without the compound.

In connection with diabetes, the method can be used to detect the ability of a chemical compound to inhibit aldose reductase. The method can be used with a glucose as a substrate and with an aldose reductase inhibitor to determine the effectiveness of the compound. The method is particularly useful for testing inhibitors in the presence of an excess of substrate for the enzyme of interest. Enzyme inhibitors are well known to those skilled in the art.

Capillary electrophoresis employs narrowbore capillaries to perform high efficiency separations of both large and small molecules based on electrophoretic migration and electroosmotic flow. Capillary electrophoresis permits rapid, efficient, sensitive, and simultaneous measurement of cellular metabolites in response to elevated glucose or other chemicals in tissue culture animal models, biopsy material and in clinical applications.

The advantages of the application of capillary electrophoresis to the study of the effects of diabetes on tissues are the following:

(1) high efficiency similar or better than high performance gas chromatography or bioassays to measure the same compounds;

(2) requires minimal sample;

(3) requires minimal sample preparation;

(4) has wider selection of analysis for similar and dissimilar compounds from the same sample run;

(5) rapid (less than one hour) quantitation from samples;

(6) much less expensive than existing assays; and (7) allows tracking of changes in a patient over time to determine the effectiveness of a treatment.

Use of capillary electrophoresis in the manner of the present invention provides the basic science researcher, clinical trial investigator or pharmaceutical company with a rapid, accurate and inexpensive determination of efficacy of therapy at the cellular level. About 90% of the products produced can be detected.

Capillary electrophoresis (CE) can measure concomitant changes in cellular metabolites known to contribute to the development of long-term complications of diabetes (see FIG. 1). Presently, no simple means are available to measure the concomitant levels of these compounds in vitro or in vivo. These metabolites include the following compounds:

| | |
|---|---|
| sorbitol | fructose |
| lactate | pyruvate |
| myo-inositol | protein kinase C |
| NADPH/NADP+ | nitric oxide |
| NADH/NAD+ | ATP/ADP |
| glucose | diacylglycerol |

Figure 2:
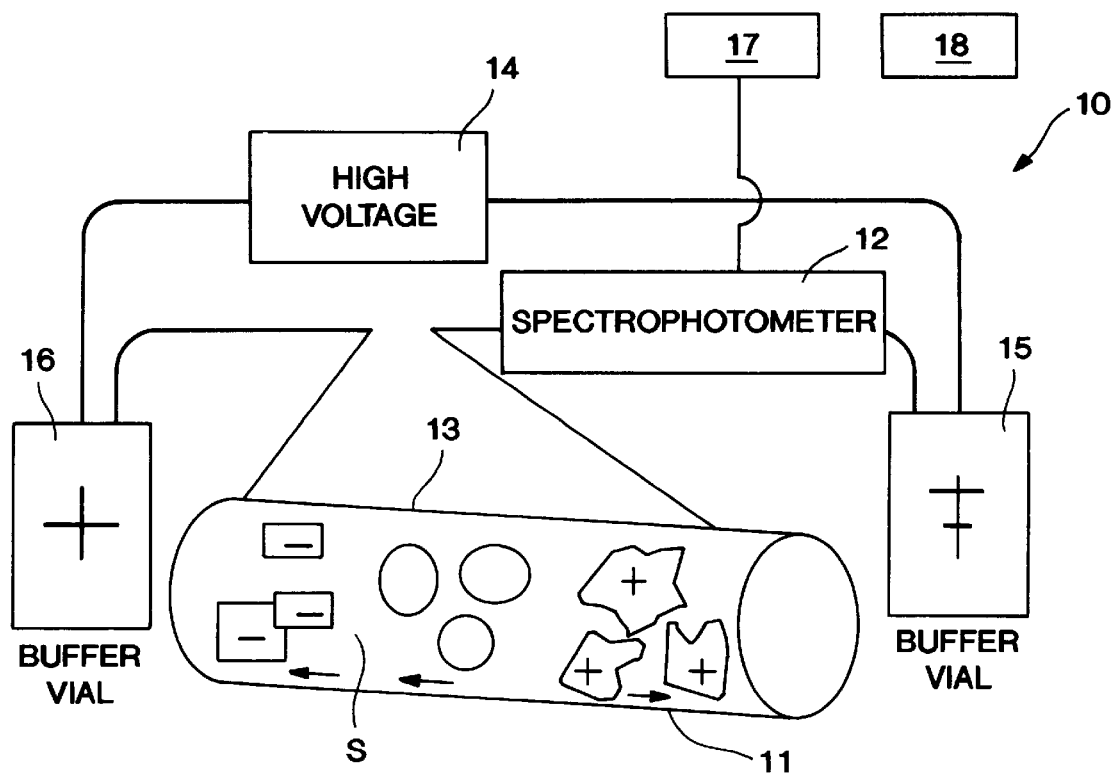
FIG. 2 is a schematic perspective view of a capillary electrophoresis (CE) device 10. CE relies principally on two forces: electrophoretic migration (net mass charge of the molecule) and electro-osmotic flow (bulk flow of buffer through a capillary tube 11). Detection is achieved by real-time monitoring using spectrophotometric detection by a spectrophotometer 12 through a window 13 in the capillary tube 11 as separated molecules pass by. High voltage 14 is used to separate molecules based on differences in net charge and size (electrophoretic migration to negative electrode 15). Electroosmotic flow moves neutral as well as negatively charged molecules toward the ground electrode 16.
Figure 11:
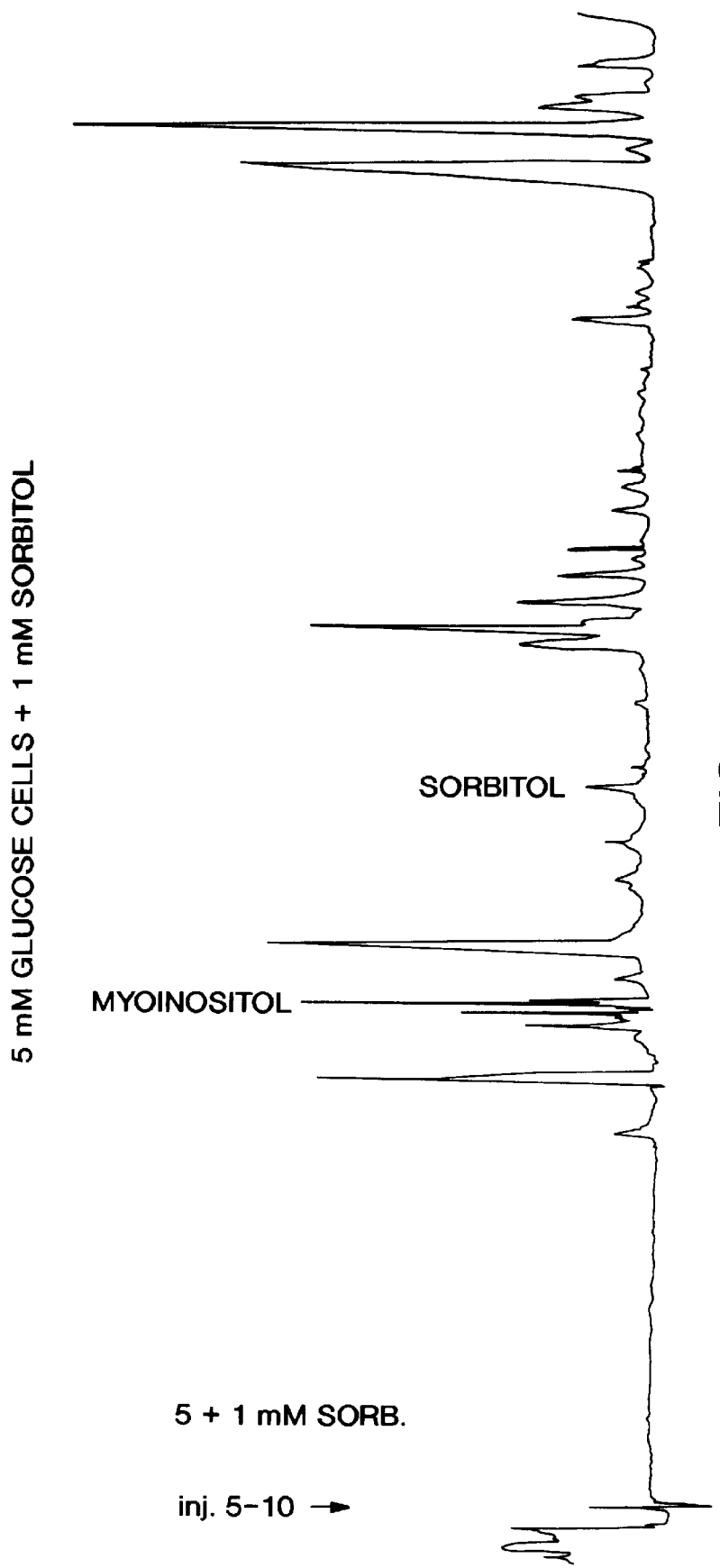
Figure 12:
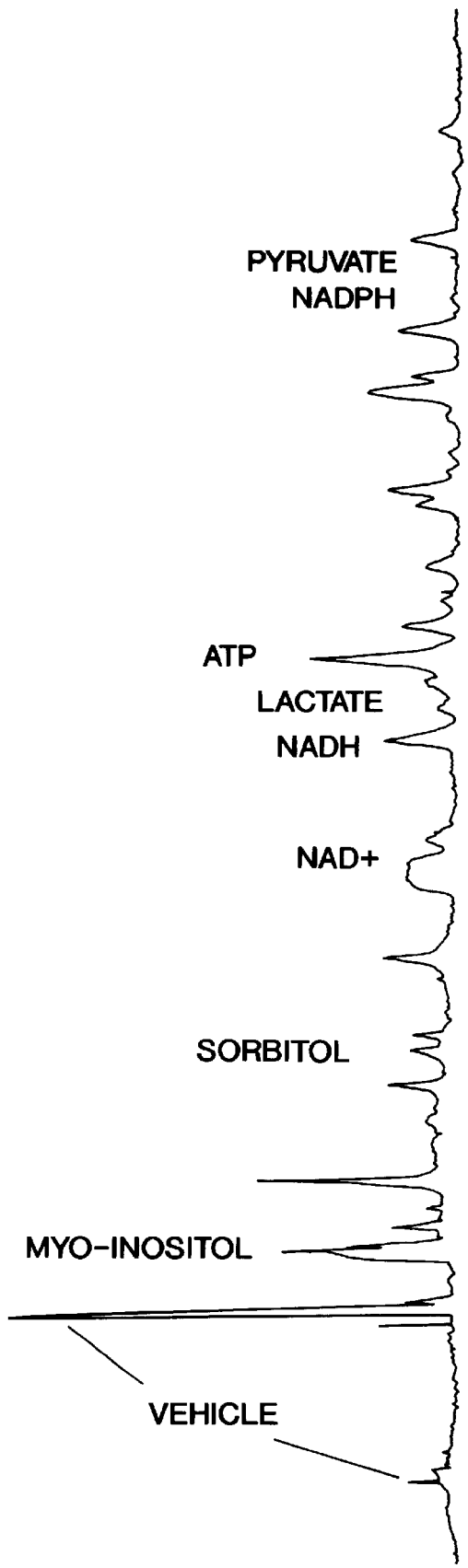
Figure 13:
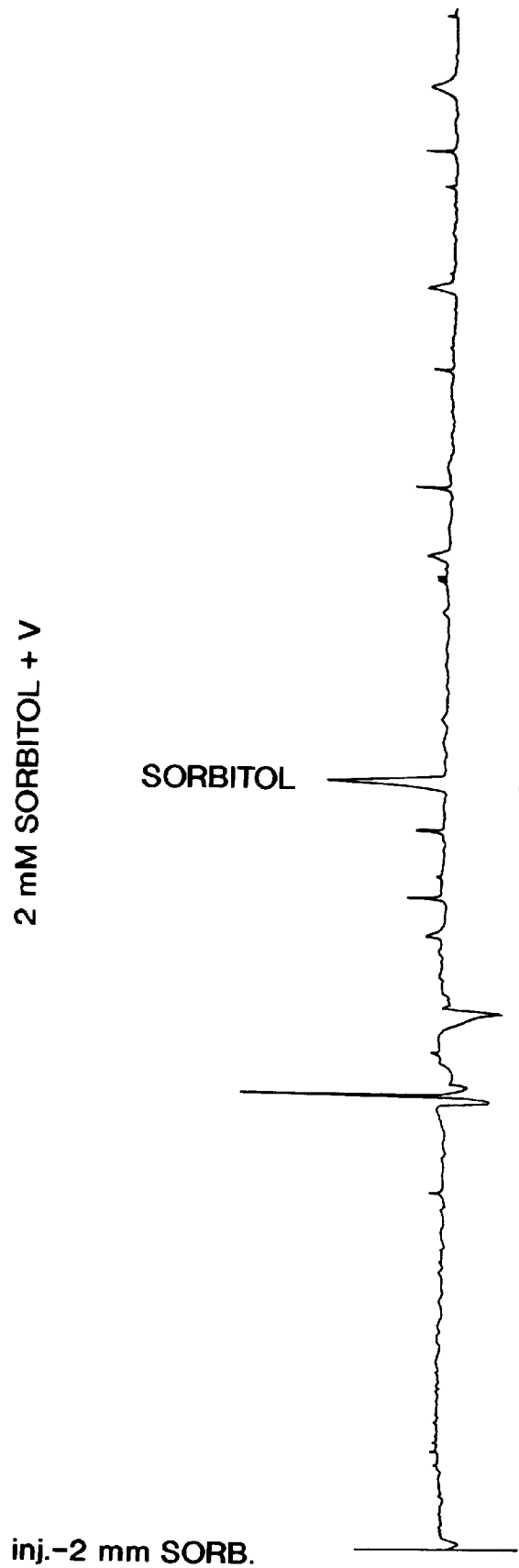
Figure 14:
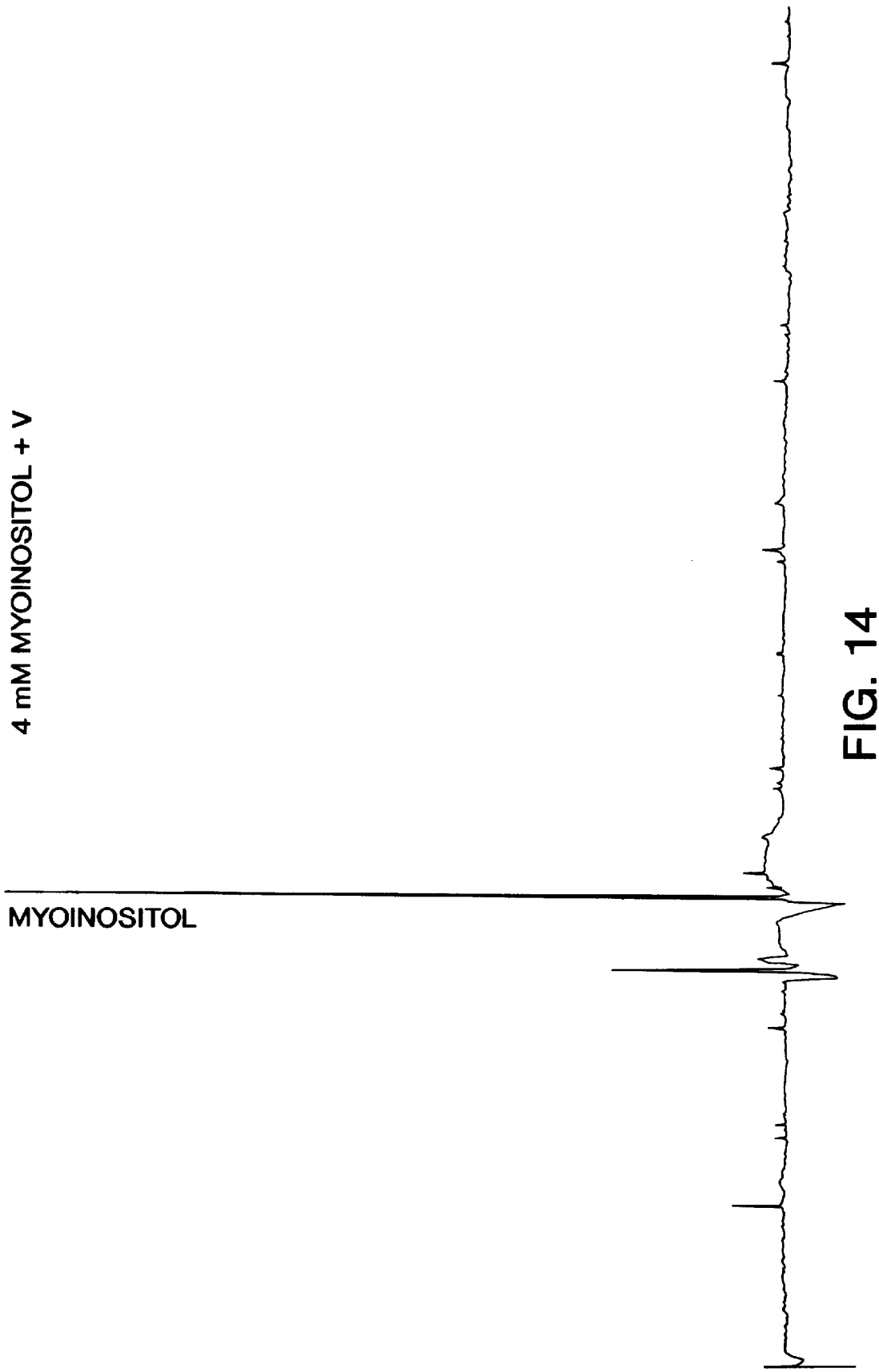
Figure 15:
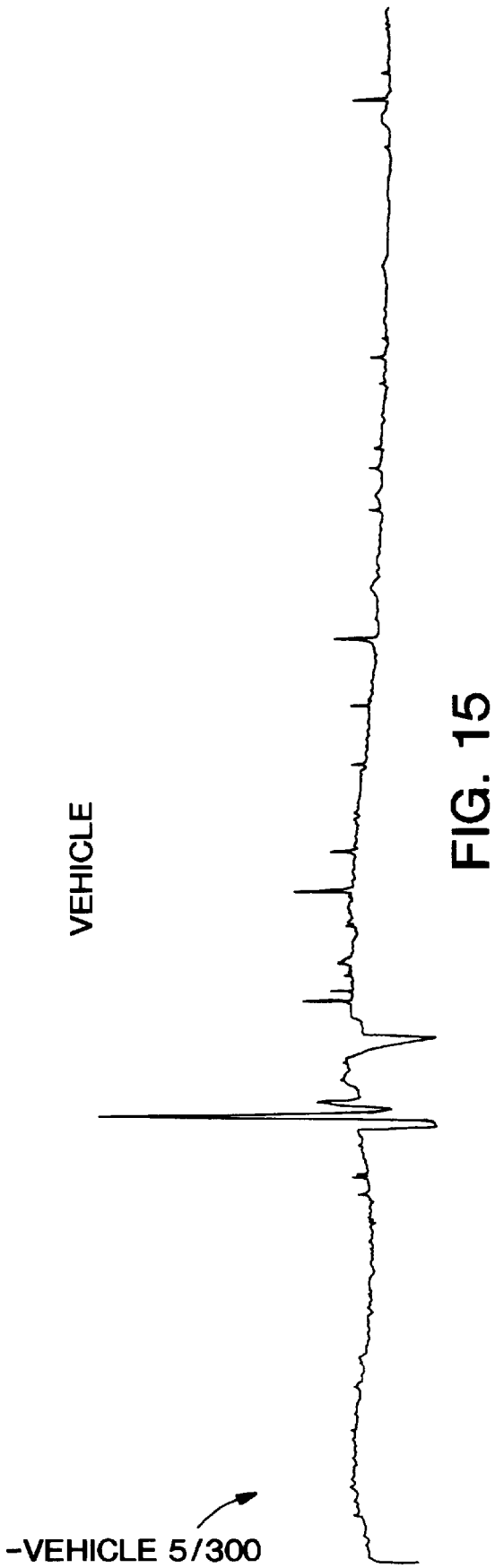

CE is a family of related techniques that employ narrowbore (20–100 $\mu$M internal diameter) capillaries to perform high-efficiency separation of both large and small molecules (see FIG. 2).

electrophoretic migration (based on the net mass charge of the molecule).

electro-osmotic flow (bulk flow of carrier buffer through the capillary tube).

Detection is achieved by real-time monitoring using spectrophotometric detection through a window in the capillary tube as separate molecules pass by (see FIG. 2). The theoretical detection of compounds is in the nanomolar range (typically ten fold greater than that commonly achieved with HPLC).

Individual capillary electrophoresis peaks have an area proportional to the concentration of the metabolite measured, corrected for the specific absorbance of that metabolite at that frequency. Odd shaped peaks result when multiple peaks have similar migration times, or when the field is not sufficiently strong to drive neutral compounds only carried by the electro-osmotic flow into a single band. When the peak height/area relation is compared using Lorentzian and Gaussian models, the data indicate that the Lorentzian model is the better fit. This is useful in that the peak height is directly proportional to the peak area for Lorentzian peaks, so that changes in peak height directly reflect changes in peak area, and thus, concentration of metabolite.

EXAMPLE 1

In order to detect metabolites of the different metabolic pathways described in FIG. 1, a unique application of capillary electrophoresis (CE) was undertaken using primary isolates of human retinal pigment epithelial cells (RPE). CE is a powerful separation and quantitation technique that often provides high resolving power, shorter analysis time, and lower operating cost than high-performance liquid chromatography (HPLC) or conventional gel electrophoresis (Xu, Y., Capillary Electrophoresis. Analytical Chemistry 67(12)463R–473R) (1995)). According to their charge, hydrophobicity, size, or stereospecificity, a wide range of biologically active molecules such as inorganic ions, organic acids, amino acids, peptides, drugs, nucleosides, nucleotides, vitamins, steroids, hormones, carbohydrates, proteins, and nucleic acids can be separated by CE (Altria, K. D., Methods in Molecular Biology 52:3–13 (1994)). CE produces high-efficiency separations of sample ions in a narrow bore (25–100 $\mu$m) capillary tube 11 that is filled with an electrolyte solution (liquid phase) S (FIG. 2). The principal components are a high-voltage power supply 14, the capillary tube 11 that passes through the optical center of a detection system including a spectrophotometer 12 connected to a data acquisition device 17, a sample introduction system (not shown) and an autosampler (not shown), all of which may be controlled by a personal computer 18 (Altria, K. D., Methods in Molecular Biology 52:3–13 (1994)). CE relies principally on two forces, electrophoretic migration (based on the net mass charge of the molecule) and electro-osmotic flow (bulk flow of carrier buffer through the capillary tube 11) (Altria, K. D., Methods in Molecular Biology 52:3–13 (1994)). Detection is achieved by real-time monitoring using spectrophotometric detection through the window 13 in the capillary tube 11 as separated molecules pass by. The theoretical detection of compounds is in the nanomolar range, typically twice as great as the detection threshold commonly achieved with HPLC (Altria, K. D., Methods in Molecular Biology 52:3–13 (1994)).

Cell Culture Methods: RPE cells are non-transformed cells easily isolated from postmortem eyes and retain well defined phenotypic characteristics for 30–40 passages in culture (Del Monte, M. A, et al., New techniques for in vitro culture of human retinal pigment epithelium. Birth Defects: original Article Series 16-327–338 (1980)). The retinal pigment epithelium is a homogeneous monolayer of cells that exhibit glucose-induced sorbitol accumulation and myo-inositol (MI) depletion correctable by the addition of an aldose reductase inhibitor (Henry, D. N., et al., J. Clin. Invest. 92(2):617–623 (1993); and MacGregor, L. C., et al., J. Biol. Chem. 261:4046–4055 (1986)). Furthermore, RPE cells demonstrate glucose induced physiological impairment like decrease rod outer segment phagocytosis in vitro or deterioration of electroretinograms in vivo, correctable by MI supplementation or AR2 inhibition (Del Monte, M. A., et al., Diabetes 40:1335–1345 (1991)). In vivo AR2 was immunohistochemically detectable in the retinal pigment epithelium in 55% of human diabetic subjects with background retinopathy and in 87.5% of individuals with proliferative diabetic retinopathy while undetectable in non-diabetic human eyes (Vinores, S. A., et al., Diabetes 37:1658–1664 (1988)). Thus, RPE cells are a pathophysiologically relevant model to study effects of elevated glucose on polyol metabolism and AR2 gene expression. Retinal Pigment Epithelial (RPE) cells were isolated as previously described (Del Monte, M. A., et al., New techniques for in vitro culture of human retinal pigment epithelium. Birth Defects: Original Article Series 16:327–338 (1980); and Henry, D. N., et al., J. Clin. Invest. 92(2):617–623 (1993)). The established RPE cell lines are passaged at a density of 10,000 cells/cm² in 10 cm dishes in Minimal Essential Medium with 2 mM L-glutamine (MEM, GIBCO, Grand Island, N.Y.) ([MI]=11.1 $\mu$M) containing 20% calf serum (CS) ([MI]=90–120 $\mu$M) and 5 mM glucose at 37° C. in humidified 95% air and 5% $CO_2$. RPE were grown for 168 hours in 5 mM (normal) glucose containing media, or media supplemented to 20 mM (pathophysiological) or 300 mM (hyperosmolar) glucose.

Preparation of Cell Analytes For Analysis by Capillary Electrophoresis: RPE were briefly washed three times with Hank's phosphate buffered saline and gently removed from tissue culture plates using a plastic policeman. Cells were pelleted and the buffer removed and then mixed with an extraction solution of either 1000 or 200 $\mu$l of 3.5% perchloric acid (PCA)/20% ethanol, shaken well and the protein was pelleted. The supernatant was removed and then neutralized with a solution of 3 M KOH/0.5M $KH_2PO_4$ in an amount 22% of the PCA/EtOH added, with a final pH of 6.8–7.2. Pelleted proteins were dissolved in 0.1 N NaOH and concentration determined using the BCA spectrophotometric assay (Smith, P. K., et al., Anal. Biochem. 150:76–185 (1985)).

Capillary Electrophoresis Methods, Detection And Ouantitation of Analytes: Experiments were performed using a ISCO (Lincoln, Nebr.) model 3850 electropherograph and performed at 20° C. In these experiments the conditions used were a 100 $\mu$m diameter capillary tube 11 of 98 cm, with 5 mm detection window at 66 cm from the injection site. The carrier buffer was 25 mM sodium borate at a pH of 9.44. The samples were vacuum injected for 2, 4 or 8 seconds at 0.5 psi ($\Delta$P). The calculation of the injection volume ($V_i$) is $$V_i = \Delta P \cdot \pi \cdot r^4 \cdot t / 8\eta \cdot L^T$$

where $\Delta$P is the injection pressure, r is the capillary radius, t is the injection time, $\eta$ is the fluid viscosity and $L_T$ is the total capillary length. For these experiments, r is 50 $\mu$m, $\eta$ is 0.01 poise, $L_T$ is 98 cm. For a 1 second injection, the injection volume is 8.63 nl. Injection volumes of 17.3 nl, 34.5 nl and 69 nl for the 2, 4 and 8 second injections used in the different experiments described here. The volume of the capillary is 7.7 $\mu$l, filling 0.22, 0.45 and 0.9 percent of the capillary volume for respective injection times. The driving voltage was 20 kV toward ground. These conditions produce a current of approximately 90 $\mu$A, rising slightly as the run progresses. Absorbance with a maximum of either 0.02 or 0.005 units was recorded at 195 nm, with risetimes of 1.6 or 0.8 s at 0.02 or 3.2 s at 0.005. Runs were recorded at 1 cm/min on an analogue recorder. The different compounds appear as a series of peaks, their migration times determined by the electroosmotic flow and their relative attraction to the anode. Ideal peaks have Lorentzian line shapes in which the peak height is proportional to the area. Peaks were identified by runs of individual compounds dissolved in neutralized extraction buffer and by addition to RPE cell extracts. Prolonged exposure of the capillary tube 11 to buffer solution results in increased run time (FIGS. 3A to 3D). Positively-charged compounds or those near neutrality have little change in run time, while there is an increase for compounds with greater negative charge/mass ratios. The capillary tube 11 is flushed with borate buffer immediately prior to sample injection and the current measured as a check for bubble formation in the tube 11. The capillary tube 11 is filled overnight with 0.1 N NaOH with the tips sealed to prevent salt formation. Soaking in NaOH returns the capillary tube 11 to its original state and reduces the run duration. All reagents were of the highest purity (HPLC grade or molecular biology grade, SIGMA, St. Louis, Mo.). Peaks for sorbitol, myo-inositol, lactate, pyruvate, NAD/NADH, NADP/NADPH, ATD, and ADP were identified by runs of individual compounds and the relative position (electrophoretic migration time) of the compounds to each other determined in both carrier buffer and cell samples.

Measurement of Analytes: Measurements of sorbitol and myo-inositol were determined from the PCA extracts kept frozen at −70° C. until assayed and then normalized to cell protein content (BCA method (Smith, P. K., et al., Anal. Biochem. 150:76–185 (1985)) Sigma, St. Louis, Mo.). Sorbitol was measured by spectrophotometric determination of NADH as fructose is formed from sorbitol by sorbitol dehydrogenase (Sigma, St. Louis, Mo. (Weissbach, A., Sorbitol Assay. In Methods of Enzymatic Analysis. H. U. Bergmeyer, Ed. Academic Press, Inc. New York 1333–1336 (1974)). Absorbance was determined at 340 nm using a SPECTRONIC 21 (Milton Roy, Rochester, N.Y.) spectrophotometer.

Sorbitol concentrations in the 5 and 300 mM RPE cell extracts were made using sorbitol standards and concentration spikes in the CE, and measuring sorbitol in the extract using the sorbitol dehydrogenase (SDH) reaction. In the latter, 50 μl of extract were added to 500 μl of 200 μM $NaH_2PO_4$ pH 7.4 buffer solution and 25 μl of 100 mM NAD. Absorbance was recorded, and 10 μl of 80 U/ml SDH added. The change in absorbance was correlated with sorbitol standards prepared in extract solution. In the example above, the CE measurement of sorbitol in the 300 mM RPE extract was approximately 1 mM, confirmed by similar SDH measurement. The signal-to-noise ratio of the sorbitol peak in the 300 mM extract is 18. There was no detectable sorbitol in the 5 mM RPE extracts in any sample using SDH. In some cells, there is another peak there co-electrophoreses with sorbitol (see the control in the sorbitol peak identification pherogram). In the 300 mM RPE cells, the relative increase in the peak size includes both sorbitol and this unknown compound. The 300 cells have 83% of the protein concentration (296 vs. 356 μg/ml) of the 5 mM RPE cells. If the unknown peak size is reduced by 17% in the 300 cells, the CE calculated sorbitol concentration in the extract is 0.4 mM, compared with 0.35 mM by SDH measurements. Given the similar readings, a major advantage CE confers in this case is that only 69 nl of extract were used for the measurement, against 50 μl for the SDH measurement, or over 700 times less. CE would thus require much less tissue than SDH for a sorbitol measurement.

Concomitant Detection of Analytes From Cultured RPE Cells. Electropherograms of RPE cells cultured in 5 mM (normal glucose), 20 mM (pathophysiological level of glucose), or 300 mM (hyperosmolar level) glucose are presented in FIGS. 3B, 3C and 3A, respectively and demonstrate at least 25 different peaks were detected concomitantly at 195 nm. FIG. 3D shows the electropherogram of 50 μl of the 5 mM sample with 2.5 μl of 50 mM sorbitol added. There is an increase in run duration of the different samples. The peak heights of the seventeen largest peaks in the two 5 mM glucose samples were compared. The peak corresponding to the extraction buffer (the largest peak on the far left) in the spiked sample had 0.99 of the height of the same peak in the unspiked sample. For the sixteen largest peaks arising from the RPE cell metabolites, the average height was 0.95±0.05 (SD, n=16). The expected height, corresponding to a change in area for Lorentzian peaks (Fukushima, E., et al., In *Experimental Pulse NMR:A Nuts and Bolts Approach*. p. 138. Addison-Wesley, Reading, Mass. (1981)) is expected to be 0.95 for the change in metabolite concentration due to dilution of the 50 μl sample by 2.5 μl from the sorbitol solution. Hyperosmolar levels of glucose were included in the experiments because this is a known inducer of aldose reductase in these cells (Henry, D. N., et al., J. Clin. Invest. 92(2):617–623 (1993)). The electromigration times of individual peaks do not vary relative to one another during repetitive runs of the same samples. The heights of individual peaks change only under the different conditions employed in each experiment and are proportional to the absolute amount of each metabolite in each sample. For comparisons between different cellular conditions the relative amounts of each metabolite must be corrected for protein content because RPE cells gown in hyperosmolar conditions have approximately 40% less protein as they grow more slowly than cells in 5 mM or 20 mM glucose. The lower metabolite peak heights in the 300 mM glucose cell samples (compare with the large first peak, part of the vehicle) reflect this rejection. Those cells grown under hyperosmolar conditions are viable, since non-viable cultures have extensive proteolysis, and the continuum of different breakdown compounds produces a continuous electrophoretic curve without separation of individual peaks (data not shown). These data dramatically demonstrate the utility of capillary electrophoresis for the concomitant detection of dissimilar metabolic analytes from complex biological systems.

Identification of Analytes. The electromigration time (position) of each compound of interest was identified and compared to the appearance of the peak in the spiked RPE samples. Examples of each of these are shown in the electropherograms, with the peak identity, injection time, absorbance and risetime included for each run (FIGS. 4A to 9C). The electrophoretic migration peak of myo-inositol was determined by the addition of 4 mM myo-inositol to the carrier buffer alone (FIG. 4A) and compared to the appearance of the same peak in RPE cells grown in 300 mM glucose (FIG. 4B), and in RPE cells grown in 5 mM glucose (FIG. 4C). Approximately 50% reduction of myo-inositol can be estimated from the electropherogram. The electrophoretic migration of sorbitol was identified by the addition of 2 mM sorbitol to the carrier buffer alone as demonstrated in FIG. 5A, and compared to the electrophoretic peak in RPE cells grown in 300 mM glucose (FIG. 5B), in RPE cells grown in 5 mM glucose and the neutralized sample spike with 1 mM sorbitol (FIG. 5C), and finally in RPE cells grown in 5 mM glucose (FIG. 5D). The electrophoretic migration of lactate was identified in RPE cells grown in 5 mM glucose and the freshly prepared neutral sample spiked with 65.2 μM lactate (FIG. 6A) and compared to the unspiked sample (FIG. 6B). Electrophoretic migration of NAD was determined by the addition of 71 μM (FIG. 7A) or 38 μM NAD (FIG. 7B) to neutralized sample from RPE cells grown in 300 mM glucose. Electrophoretic migration peaks for NAPDH and pyruvate were identified by the addition of 4 μM NADPH (FIG. 8A) or 38 μM pyruvate (FIG. 8B) to neutralized sample from RPE cells grown in 5 mM glucose (FIG. 8C). ADP and ATP electrophoretic migration peaks were determined by the addition of 4.5 mM ADP or 1.5 mM ATP to carrier buffer or neutralized sample from RPE cells grown in 20 mM glucose (FIGS. 9A to 9C).

Capillary electrophoresis has the ability to concomitantly detect chemically unrelated molecules from complex biological systems. Capillary electrophoresis has been successfully employed to the study of glucose mediated cellular perturbations in RPE cells. Approximately 25 peaks were concomitantly detected on the electropherogram including sorbitol, myo-inositol, lactate, pyruvate, ATP, ADP, NAD, NADH, NADP and NADPH. An 18 fold increase in sorbitol (confirmed by enzymatic assay) and a 50% reduction of myo-inositol has been detected when RPE cells are grown in hyperosmolar concentrations of glucose. The results of capillary electrophoresis in this cell model are highly reproducible, precise and require minimal volume (45 nanoliters), minimal time from preparation to analysis (one hour) and can be automated.

Enzymatic methods of measuring tissue metabolites typically use 50 μl of tissue extract for a single measurement. The development of a measurement technique that substantially reduced the volume of extract required means a much smaller tissue sample was needed. For a 50 nl injection using capillary electrophoresis, approximately 5 nl or 5 μg of tissue was necessary. A biopsy needle of 40 μm radius takes only 1 mm of tissue to meet this requirement. A single 10 μl drop of blood would produce 2000 identical samples. The reduction in required volumes demonstrates the applicability of CE to metabolite measurement. In addition, a technique that allowed simultaneous measurement of over 20 metabolites would reduce the time and effort required for individual measurements of those metabolites. As the FIGS. 3A to 9C above demonstrate, each electropherogram produces a quantitative measurement of multiple compounds. The combination of minimal time utilization, minimal volume, and multiple metabolite measurement makes this technique a significant improvement over current methods.

The consistency of metabolite measurement between different runs indicates the consistency with which CE can be used for biological measurements. The variation in run duration can be minimized using NaOH washes at the cost of the time required for the wash and flush of the NaOH. Variations in run duration are steepest in the slowest migrating compounds with strong negative charge/mass ratios but minimal in those compounds with positive or neutral charge/mass ratios. Calculations of concentrations using peak areas must, therefore, take into account the relative time a compound requires to pass the detection window in different runs in addition to the absorbance of each compound at the measured wavelength. Optimization of CE measurement of biological compounds of interest requires systematic variation in carrier buffer concentration type, concentration and pH, as well as capillary type, length, temperature, and polarity. Alteration of the wavelength of the absorbance measurement can prove easier for separating two co-migrating analytes than altered physical conditions in some cases. Ultimate identification of each metabolite and unidentified peaks requires independent assays for each compound of interest and/or the use of mass spectroscopy linked to the CE device presently commercially available from CE manufacturers. Validation of CE is similar to that employed for HPLC methods (Altria, K. D., et al., Electrophoresis Nov; 16(11):2143–2148 (1995)). Accuracy of CE can be determined using an alternative test for the analyte of interest followed with determinations of recovery if there is concern of loss of analyte in the CE tube matrix. The precision of CE is dependent on the method employed to measure the analytes and the optimization of conditions used to detect the analytes of interest. Given identical sample preparation methodology and buffer and capillary specifications, the reproducibility of CE will depend on usage of a specific capillary tube 11, the instrument employed, variance of cell culture and animal physiology (Kasicka, V., et al., Electrophoresis Nov; 16(11):2034–2038 (1995); and Chang, H. T., et al., Electrophoresis Nov; 16(11):2069–2073 (1995)). As is immediately apparent from FIG. 1, the consistency of the metabolite profiles from RPE cells, even though grown under different conditions, increases confidence in the application of capillary electrophoresis to RPE metabolite measurement. The application of capillary electrophoresis to the study of cell and tissue damage from diabetes holds great promise in advancing the basic science and translatable discoveries related to glucose metabolism and long-term complications of the disease. This process should be transferable to tissues from humans with minimal invasiveness and maximal information content.

CE is an effective methodology to study concomitant changes in cellular metabolites related to long-term complications of diabetes. CE is accurate, easy to perform, and reproducible with minimal sample preparation (15 minutes) and volume. Samples are run on electropherograph in approximately 35 minutes.

CE is a valuable method for research and clinical applications to study diabetes and other diseases. Immediate applications would include:

determination of aldose reductase and PKC inhibitor efficacy in vitro and from tissue biopsy specimens;

accurate, real-time measurements of changes in glucose metabolic intermediates, polyol metabolism, and changes in cellular redox state; and automated screening of large libraries of compounds for pharmaceutical development related to diabetes and other disease therapy.

EXAMPLE 2

Capillary electrophoresis was used to study the effects of elevated glucose in human retinal pigment epithelial (RPE) cells in vitro. RPE cells exhibit glucose-induced, aldose reductase inhibitor-sensitive physiological impairment manifested by sorbitol production and myo-inositol depletion. RPE cells were grown in 5 mM or 300 mM glucose for 48 hours then harvested. Cells were mixed with 3.5% perchloric acid/20% ethanol (v/v) then neutralized with 3M KOH-phosphate buffer. Protein was removed by centrifugation. The supernatant was vacuum injected for 4 seconds into a 10 cm long, 100 μm diameter capillary. The injection volume was approximately 35 nanoliters. The sample, in an ISCO model 3850 electropherograph, migrated from positive to ground using 25 mM borate buffer, pH 9.5 as the carrier. The driving voltage was 20 kV constant, at approximately 90 μA. The individual peaks were detected at 195 nm with an absorbance of 0.02 units and a rise time of 1.6 seconds. Peaks were recorded at 2 cm/min and 1 V maximum. The entire sample run required 35 minutes. Approximately 25 peaks were concomitantly detected on the electropherogram including sorbitol, myo-inositol, lactate, pyruvate, ATP, ADP, NAD, NADH and others. An 18 fold increase in sorbitol (confirmed by enzymatic assay) and a 50% reduction of myo-inositol in RPE cells grown in 300 mM glucose vs. 5 mM glucose. Tentatively, there appears to be reciprocal changes in cellular lactate, pyruvate and NAD, NADH levels in response to high glucose. The results are shown in FIGS. 10 to 15.

EXAMPLE 3

This Example describes a method for the measurement of tissue metabolites from rabbit urinary bladder using capillary electrophoresis (CE) which has been developed. The method generates a reproducible electropherogram containing more than twenty peaks from less than 20 nanoliters of extract solution generated from 1.1 nl (or approximately 1.2 micrograms) of tissue in less than 40 minutes. Multiple samples from the same bladder produce standard errors comparable to enzymatic or NMR measurements of metabolites: phosphorus NMR measurement requires $10^6$ more tissue than CE; individual enzymatic measurements using 100 µl per sample requires 2000 µl, $10^5$ greater volume than CE requires for the same number of metabolites. CE detects about 3 times more peaks than phosphorus NMR on a similar time scale. Comparable measurements using enzymatic analysis would require approximately 10 times longer. The combination of minimal tissue volume requirements, rapid measurement, and reproducibility makes CE a valuable tool in the investigation of simultaneous changes in multiple metabolites from minute tissue samples.

In the course of using capillary electrophoresis for protein biophysical studies, similar to those of Lee and Yeung (Lee, T. T., et al., Anal. Chem. 64:3045–3051 (1992)), it became apparent that the minimal volume required for detection made CE amenable to the measurement of tissue metabolites. A glass tube of 50–100 micron diameter was used. The sample travels by electroosmotic flow through the tube using a carrier buffer driven by a high, 5–30 kV, voltage. The buffer is moved toward ground, and carries the sample compounds by bulk flow. The sample compounds separate from one another based on their individual charge-to-mass ratio, with those whose charge is the same as the driving voltage moving faster than the carrier buffer, while those with the opposite charge having their movement retarded by their attraction to the high voltage end of the tube. The sample compounds are detected at a given wavelength as they pass a window near the ground end of the tube.

The minimal volume and time required for CE stand in contrast to other methods used for measurement of tissue metabolites. The CE methods can measure more than 20 compounds in less than one hour with no chemical modification, and require only 1.2 µg or 1.1 nl of tissue. For spindle-shaped smooth muscle cells of 200 µm length, the total number of cells needed varies from 15–60 cells, corresponding to average cell diameters of 5–10 microns This tissue volume is far less than any biopsy sample or the amount of tissue in a 96-well culture plate. Both enzymatic and NMR methods of detecting metabolites from the rabbit urinary bladder (Kushmerick, M. J., et al., J. Biol. Chem. 261:14420–14429 (1986)) were used Enzymatic analysis requires the use of approximately 100 µl of extract solution and 0.5 hours for the measurement of each metabolite: 20 metabolites would require at least 10 hours and 2000 µl of extract. Phosphorus NMR has the advantage of measuring metabolites in living cells, but requires 1 gram of tissue and 1 hour of measurement for smooth muscle, and then can only measure those compounds that contain phosphorus.

Methods

Tissue Procedures. Male, adult New Zealand white rabbit were anesthetized and euthanized by University Laboratory Animal Resource personnel using Fatal Plus (392 mg/ml sodium pentobarbital). The abdomen was opened and the urinary bladder excised. The bladder was placed in ice-cold isoosmolar NaCl. Tissue samples with a weight of 5.6±0.12 mg, SD, N=3 from the first rabbit and 5.1±0.96 mg, SD, N=4 from the second rabbit were cut from the body of the bladder. The tissue sample was placed in 60 µl of extraction solution containing 3.5% perchloric acid/20% ethanol and stirred well for two minutes. The extract was then neutralized with 13.2 µl of 3.0 N KOH/0.5 M $KH_2PO_4$, with a final pH of 6.8–7.2. This procedure precipitates potassium perchlorate, which is then spun to the bottom of the sample tube using a table top centrifuge. A sample volume of 45µl was withdrawn from the centrifuged tube and placed in a CE sample vial.

CE methods. An ISCO (Lincoln, Nebr.) Model 3850 electropherograph was used at 20° C. for these experiments. The capillary tube of 100 micron diameter, 98 cm long connected two reservoirs containing 25 mM sodium borate, pH 9.44. The capillary contains a detection window 66 cm from the 20 kV anode. Compounds were detected at 195 nm, at absorbance detection ranges from a full scale of 0.02–0.5 absorbance units and a risetime of 1.6 s, and were recorded on a chart recorder (The Recorder Company, Houston, Tex.) at 1 cm/min with 1 volt full scale. The capillary is flushed with 0.2 N NaOH prior to injecting the initial sample of the day, and at different times prior to subsequent injections. This flushing coats the glass surface of the capillary with $Na^+$. Samples were injected for 2, 5, 10, 20 or 50 seconds using 0.5 psi (ΔP) vacuum injection. The capillary is flushed with carrier buffer and checked for current integrity prior to each injection. The calculation of the injection volume ($V_i$) is $$V_i = \Delta P \cdot r^4 \cdot t / 8\eta \cdot L_T$$

ΔP is the injection pressure, r is the capillary radius, t is the injection time, η is the fluid viscosity and $L_T$ is the total capillary length. For these experiments, r is 50 microns, η is 0.01 poise, and $L_T$ is 98 cm. The injection volume is 8.63 nl/sec. For these experiments, the injection volumes are 17.3, 43.2, 86.3, 173, or 432 nl. The capillary volume is 7.7 µl. The different injection volumes fill 0.22, 0.56, 1.1, 2.2, and 4.4 percent of the capillary. All experiments were run using 20 kV constant driving voltage toward ground, and generated a current of 78 µA. Peaks were identified by the addition of 1–2 µl concentrated metabolite to the 45 µl extract sample. Creatine, NAD, lactate, uridine-diphospho-glucose (UDPG), NADH, phosphocreatine (PCr), ADP, ATP, GTP, and UTP peaks were identified.

The 47 individual runs in this study using tissue extracts required a total of 2.04 µl of extract derived from 124 nl of tissue. Assuming a tissue density of 1.05 g/ml, this corresponds to 131 µg of tissue for the entire series of experiments.

Comparisons between samples were made using a two-tailed Student's t-test with a p<0.05 considered to indicate significant difference. Correlations were determined using linear least-squares regression analysis.

Results

Figure 16:
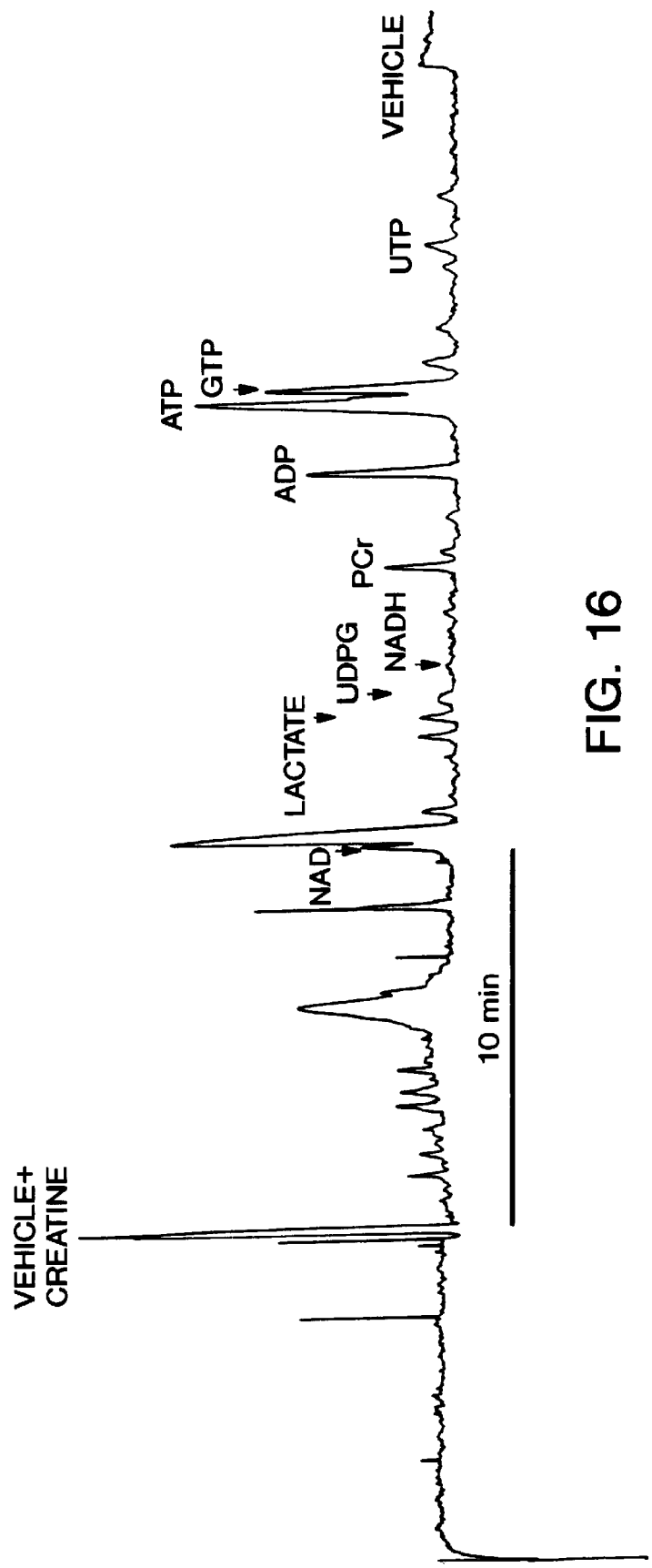
FIG. 16 is a graph of capillary electropherogram of rabbit bladder extract. The identified peaks were determined by the addition of standard to the bladder extract.

FIG. 16 shows the electropherogram (EPG) from a 2 second injection. The different peaks were identified by the addition of known standards to the extract solution. There are no standard additions to this EPG, which was generated from 1.1 nl or 1.2 µg (assuming a density of 1.05 g/ml) of bladder tissue. Positively charged compounds appear first, followed by neutral and acidic compounds, respectively. The peak sizes were compared to peaks generated by known standards at 195 nm and the relative size of the peaks is in good agreement with other methods of measuring these metabolites from this tissue (Kushmerick, M. J., et al., J. Biol. Chem. 261:14420–14429 (1986)). Very sharp spikes in the EGP, such as those to the left of the "Vehicle+Creatine" peak or to the left of NAD do not represent chemicals, but are thought to be microbubbles generated by the high voltage. They appear occasionally but not in the same place. The large vehicle peak at the start and the plateau vehicle peak on the right bracket the tissue metabolites. No peaks are ever detected beyond the plateau-shaped peak.

Figure 17A:
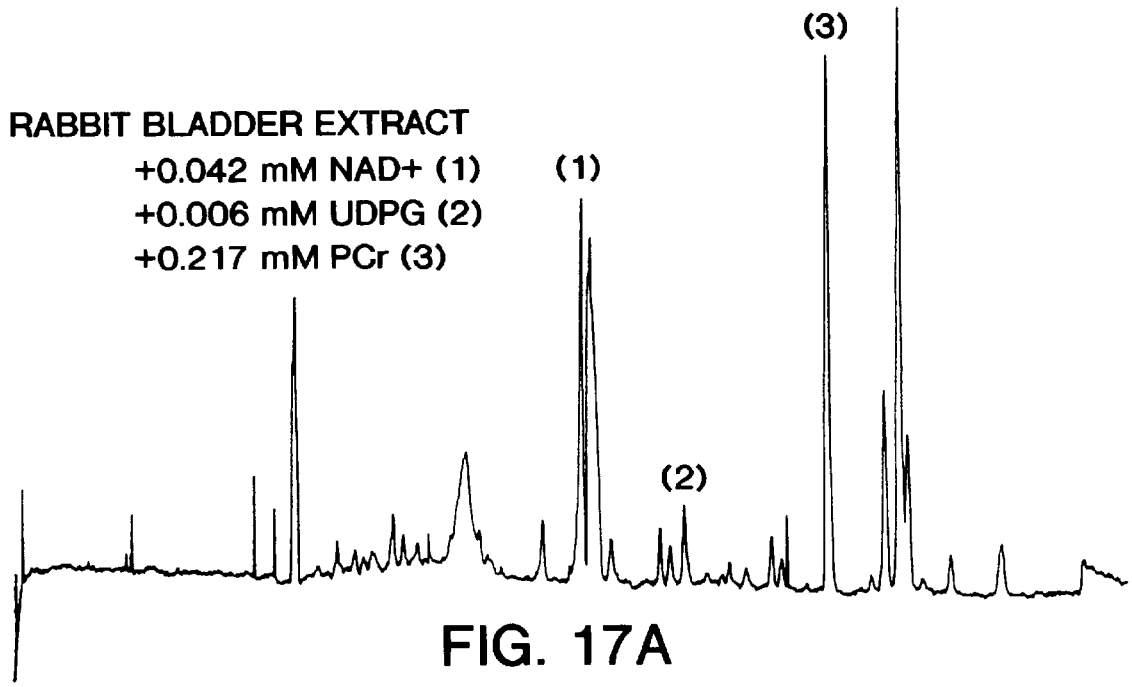
FIGS. 17A, 17B and 17C are graphs of examples of the addition of standard to electropherograms of rabbit bladder extract. The size of peaks 1, 2 and 3 can be compared to the same peaks in FIG. 16.
Figure 17B:
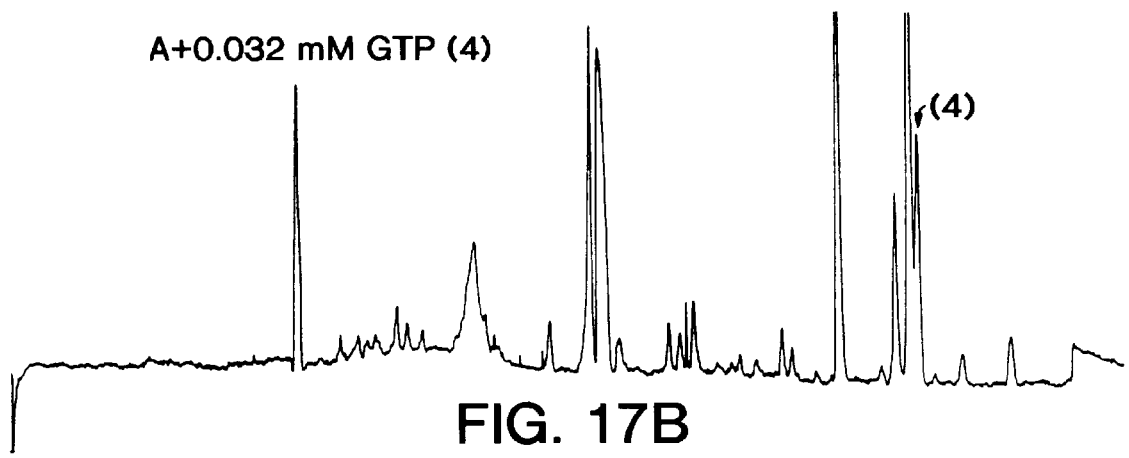
Figure 17C:
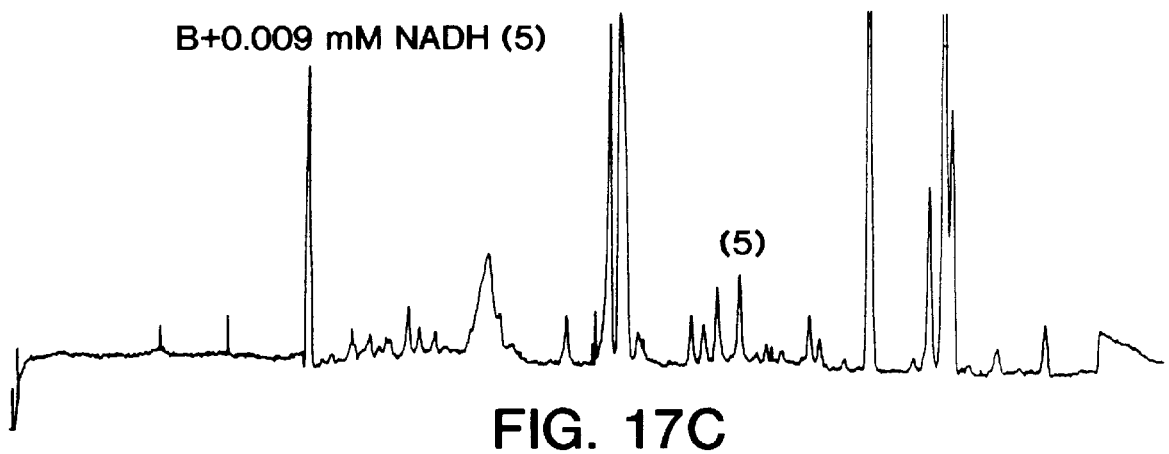

Examples of the standard spiked samples are shown in FIG. 17. In the first EPG at the top (A), NAD, UDPG and PCr have already been added, and their greater height compared with FIG. 16 is clear. In B, GTP has been added to the solution from A, and the peak indicated shows a large increase in size when compared with the same peak in A (FIG. 17A). Likewise, NADH was added to B (FIG. 17B), and there is a large increase at the indicated position in C (FIG. 17C). The other peaks identified in FIG. 16 were similarly determined.

Figure 18:
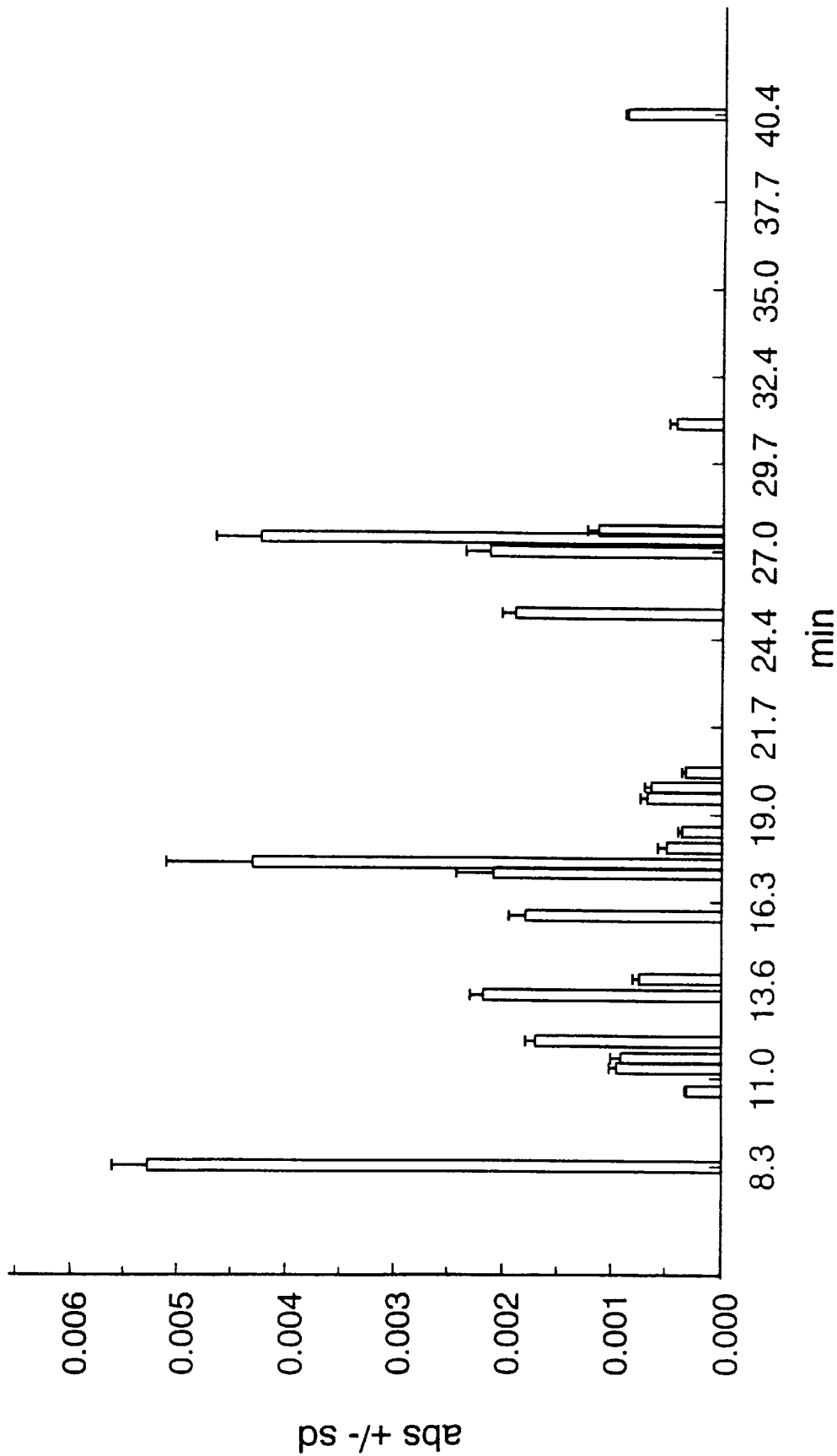
FIG. 18 is a bar graph showing reproducibility of a single sample using CE. The same rabbit bladder extract sample was run five times and the mean±standard deviation determined. The time in minutes corresponds to the time taken for each peak to appear in FIG. 16.
Figure 19:
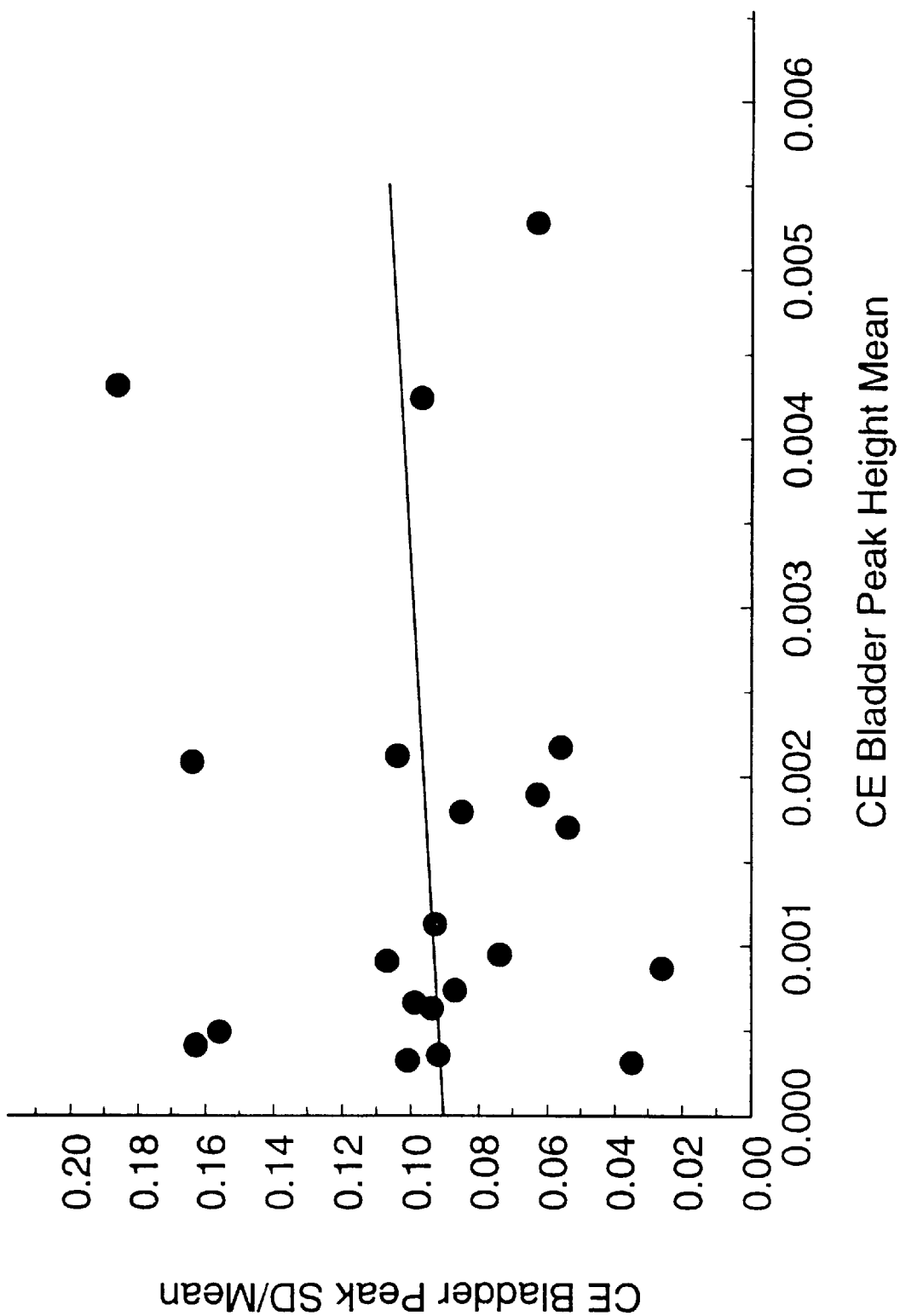
FIG. 19 is a graph showing ratios of the standard deviation/mean peak height as a function of the peak height from FIG. 18. There is no correlation between the height and the relative size of the error, indicating that the noise in the system is not unduly effecting the smaller peaks.

The consistency of measuring metabolites with CE was tested in three ways: (i) how reproducible is an individual sample; (ii) how reproducible are different tissue samples taken from the same bladder; and (iii) how comparable are different samples taken from the bladders of different animals. The first of these tests is shown in FIG. 18. A single sample was run 5 times and the peak heights measured. The sample run duration, i.e. the time until the vehicle plateau peak appeared, varied from 38–42 minutes. This time listed is for the middlemost run. A comparison of the standard deviation as a fraction of the peak height mean for each peak is shown in FIG. 19. There was virtually no slope when this data was plotted as a function of peak height, indicating that the recording noise did not unduly influence smaller peaks. The size of the error in these measurements is comparable to that of bladder metabolites measured using NMR or enzymatic analysis (Kushmerick, M. J., et al., J. Biol. Chem. 261:14420–14429 (1986)).

Figure 20:
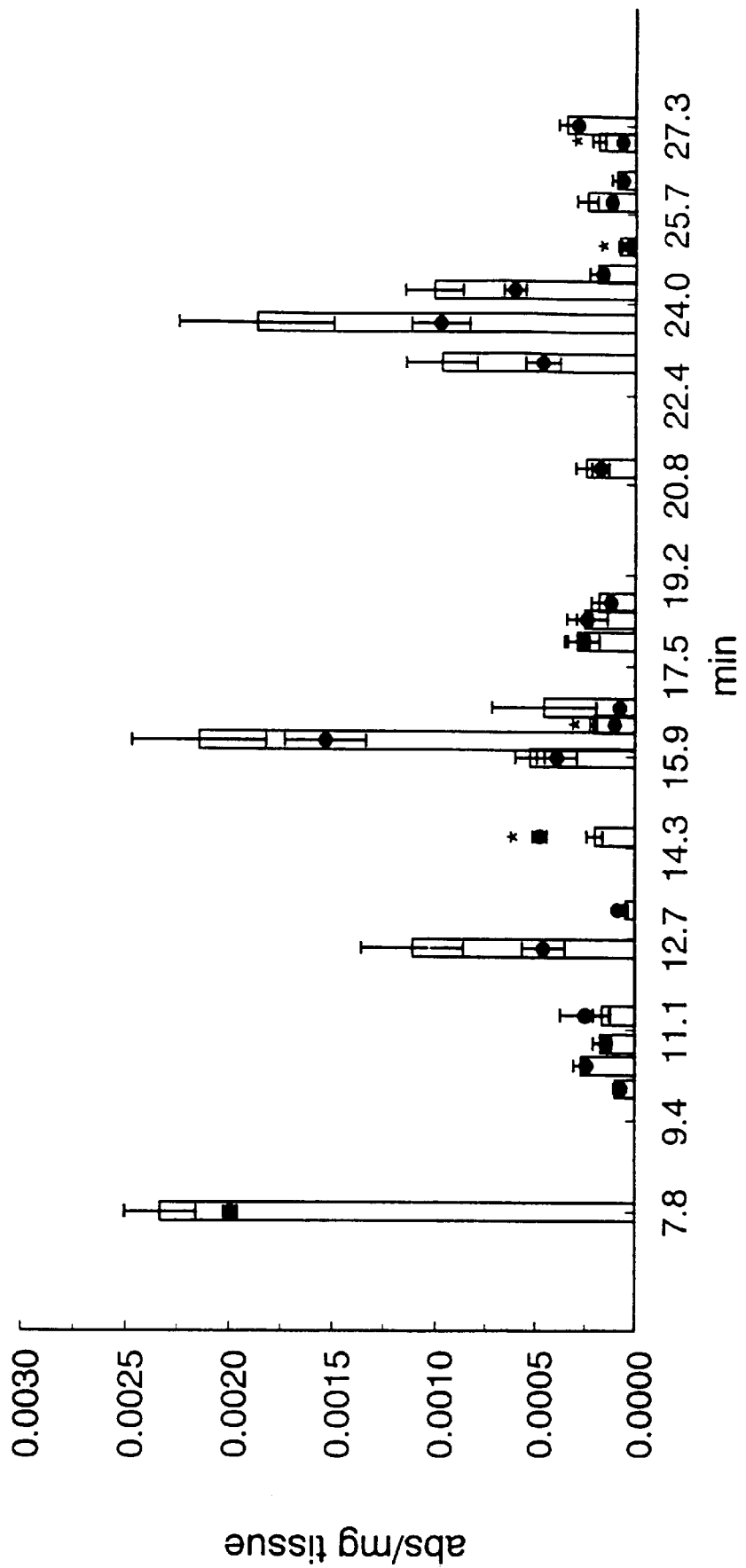
FIG. 20 is a bar graph showing a comparison of the peak sizes between tissue samples taken from the same rabbit bladder and those taken from a second bladder. The bars are the mean±SE, N=4, from one rabbit and the circles represent the mean±SE, N=3, from a second rabbit. The * indicates that the measurements between the two rabbits were different with $p<0.05$.

Comparisons of different tissue samples from the same bladder and between bladder tissue samples from different animals are shown in FIG. 20. The bar represent the peaks from one animal and the circles from the second. Again, the error signals produced are comparable to those measurements using other techniques. The general pattern of peaks was the same from both animals; this can be appreciated by comparing FIG. 15 with the top EPG from FIG. 21, both of which were 2 second injections. Four peaks, indicated by the * in FIG. 20, were found to be significantly different from one another. The identity of these peaks is not known.

Figure 21:
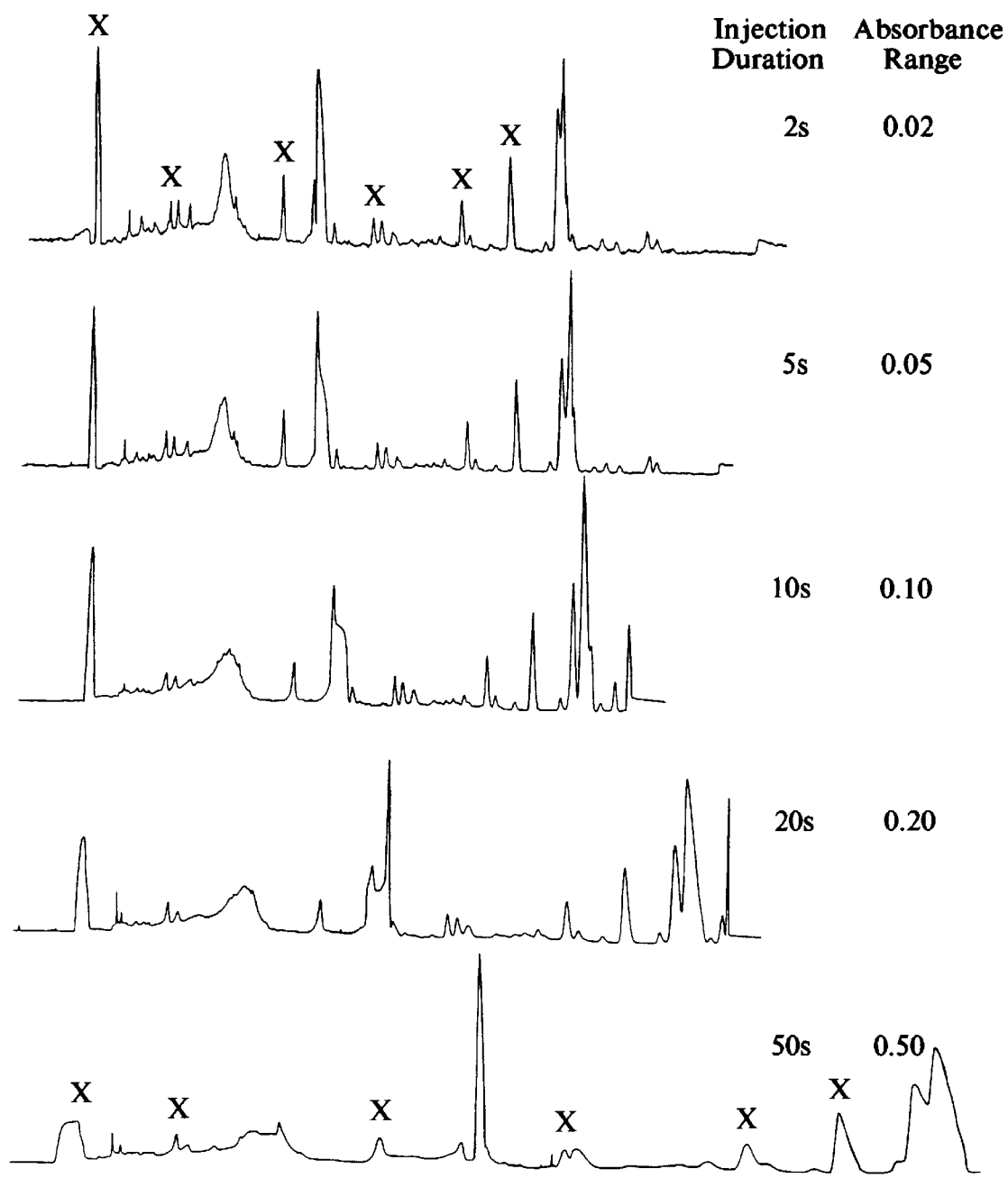
FIG. 21 are electropherograms of the same rabbit bladder extract sample injected for different durations and recorded at different absorbance ranges. Ideally all the EPGs should look identical, but the longer duration injections surpass the capillary's ability to concentrate the metabolites and the peaks are lower and broader.
Figure 22:
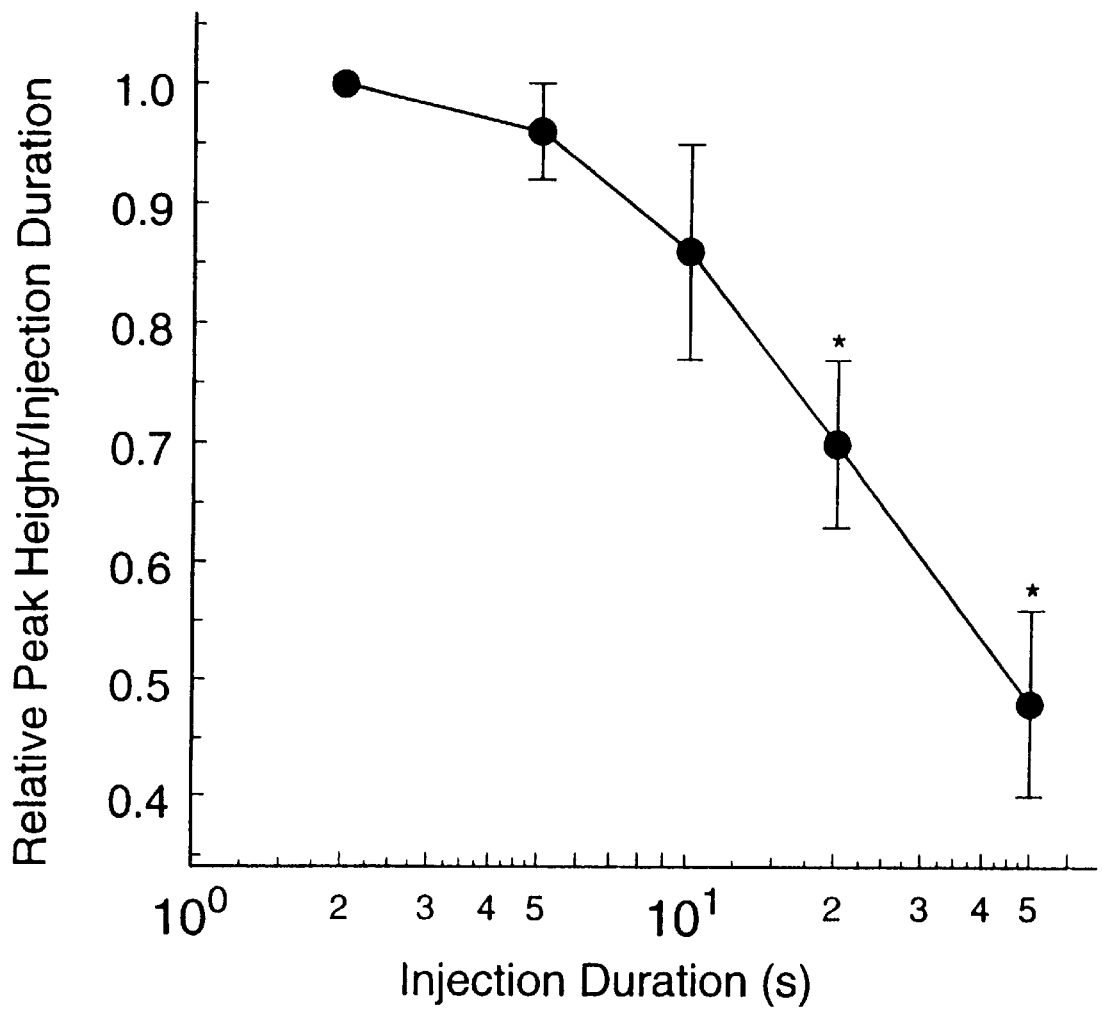
FIG. 22 is a graph of the six peaks designated by a "X" in FIG. 21 which were measured relative to the 2 second injection height and the mean±SE plotted relative to the injection duration. The * indicates the mean is significantly different from the 2 second mean with $p<0.05$.

The influence of the size of the injection duration, and thus injection volume, on the EPG profile was measured in FIG. 21. As the injection volume was increased, the sensitivity of the absorbance range was decreased, so that if there were no effect of the injection volume, all the EPGs should look identical. In fact, there is a decrease in peak height throughout the EGP, with the peaks broadening in the larger injection cases. This demonstrates the limitation of the capillary in concentrating individual metabolites. Six peaks that could be followed through all the runs were selected and their relative change in peak height determined as a function of the injection time. These averages are shown in FIG. 22. All are compared to the 2 second injection height. If there were no effect of injection duration, the plot would show a straight line across at 1.0. In fact, there is a steady decline in peak height, with the averages at 20 and 50 second injections being significantly lower. This indicates an upper limit on the useful injection time.

Note also that the 50 second injection duration EPG in FIG. 21 takes much longer to complete its run past the detector than the others. The rate of electrophoretic movement is a function of the charge on the capillary tube. Acidic compounds leach sodium from the glass walls of the capillary, altering the electroosmotic flow of the carrier buffer and the electric field the metabolites see during the run. When using large injection volumes, the amount of the acidic compounds presented to the capillary is great, significantly lengthening the run time. The capillary can be returned to its original state and the run time reduced by flushing with NaOH. If the run time has been elongated by high acid concentration, large injection volumes, or a large number of runs, subsequent injections will also have elongated run times. This was demonstrated in FIG. 23.

Figure 23:
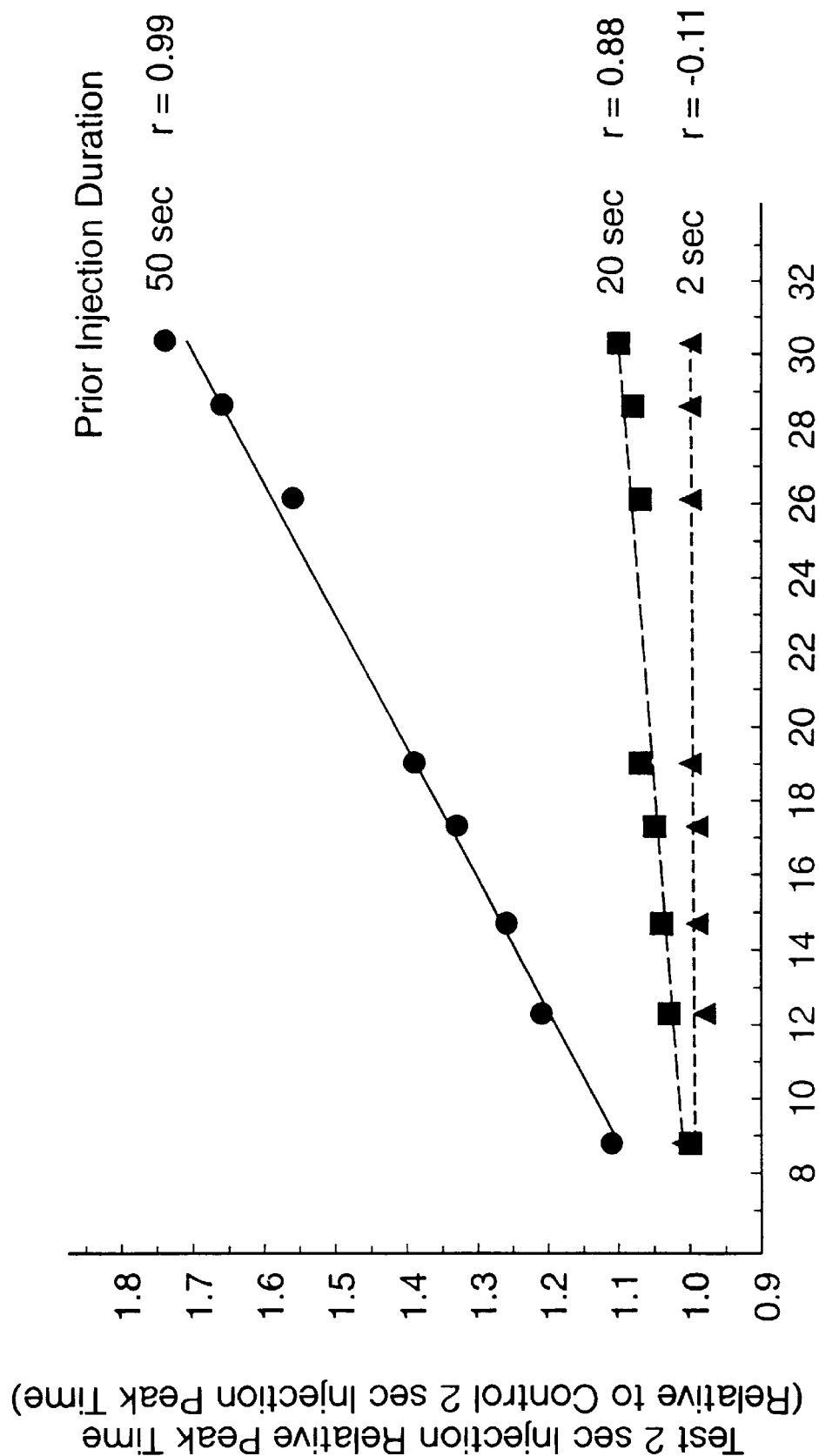
FIG. 23 is a graph showing the relative change in the time a peak from a "test" 2 second injection takes to reach the detection window relative to a control 2 second injection. The test 2 second injection followed a prior injection and run of variable duration of 2, 20 or 50 seconds. The longer the prior injection duration, the longer the peaks take to reach the window for the 20 and 50 second durations. The correlation coefficients (r) indicate that the more negative the charge-to-mass ratio of a peak, the more it will be effected by the prior runs in the capillary. Equilibration of the capillary with 0.2 N NaOH eliminates this elongation effect.

In this experiment, injection runs of different durations were made, followed by a second injection and run of 2 seconds. The capillary was equilibrated with 0.2 N NaOH for at least 1 hour prior to the first injection. FIG. 23 shows the effect of the injection duration (and volume) on the SECOND run. The relative time a peak took on the second 2 second injection run was compared with the time that peak took on a control 2 second injection run following NaOH equilibration. For a 2 second run following a 2 second run shown in the triangles, there was virtually no change in the run time. There is a linear increase in the time the 2 second injection takes following a 20 second injection run, when compared with the control 2 second injection run. Injections of 5 and 10 seconds produced peak times for the following 2 second injection between 2 and 20 second injections, but were not included in the figure. A 50 second injection produces a large change in a following 2 second injection. The acidic peaks, taking a longer time in many cases, require even greater time for the peaks to appear. This is consistent with acidic compounds leaching sodium from the capillary wall and exposing negatively charged sites. These would repel the entry of the negatively charged metabolites into that local area of the capillary and increase the run time. The fact that those metabolites with the most negative charge-to-mass ratio, such as ATP, are most effected bears this out. Experience has shown that when many runs, ten or more, are made without NaOH flushing and equilibration, even those of 2 second injections, there is a slow increase in the run time. NaOH restores the faster run time, either following many small injections or an injection of long duration.

Discussion

The use of capillary electrophoresis produces analysis of tissue metabolites that is both faster and more sensitive than other metabolic measurement techniques. Even the smallest biopsy sample would produce more than enough material for hundreds of repetitions of the same sample. The same degree of error both within and between samples means that duplicate measurements of a given sample should produce an average value within 5% of whatever the "true" concentration may be. The technique would also be amenable to testing tissue culture samples, as fewer than 100 cells were needed for the 2 second EPGs in this study. Other cell types with smaller cells than bladder smooth muscle may require more cells, but this technology promises further developments in maximizing signal from even smaller samples. For some metabolites, measurement from a single cell is not out of the question.

Even a cursory examination of FIG. 16 shows that more than 20 peaks have not been identified. The opportunity presented here includes the identification and subsequent measurement of these compounds under different conditions. Some of these compounds are present in very high amounts, but the ability to measure the smaller peaks is equally attractive. The use of longer capillaries will produce further separation of the peaks, though at a cost of longer run times. Other parameters, such as increased driving voltage or different carrier buffers can maximize the measurement of particular parameters.

This methodology is easily adaptable to any cellular system. Preliminary EPGs of several cell types (data not shown) have been made including vascular smooth muscle cells and renal mesangial cells. Each generated a reproducible EPG with characteristic peaks different from the other cell types. The use of capillary electrophoresis in the measurement of metabolites can almost certainly be extended to examine tissue proteins as well. The orders of magnitude decrease in the amount of tissue and time required for analysis when compared with other techniques demonstrates the advantages of capillary electrophoresis.

It is intended that the foregoing description be only illustrative of the present invention and that the present invention be limited only by the hereinafter appended claims.

We claim:

1. A method for quantitatively testing a chemical compound in vitro for effectiveness in altering enzyme activity of at least one enzyme in mammalian cells involved in a disease by measuring multiple enzymatic products present in the cells which comprises:

(a) treating said mammalian cells in a culture medium in vitro with the chemical compound to be tested;
   (b) separating the treated cells from the culture medium;
   (c) disrupting the cells in a fluid medium to produce an admixture of cellular debris consisting of a solid phase, and a liquid phase which contains the multiple enzymatic products;
   (d) removing the debris from the liquid phase;
   (e) subjecting the liquid phase to capillary electrophoresis in a single run wherein the multiple enzymatic products produced by the enzyme are separated;
   (f) continuously scanning the multiple enzymatic products separated in step (e) by the capillary electrophoresis with a spectrophotometer which measures light absorbance to produce a chart with peaks of light absorbance for each of the multiple enzymatic products; and
   (g) determining the effectiveness of the compound in altering the enzyme activity by comparing the peaks of the multiple products to the peaks produced from a control consisting of cells not treated with the compound.

2. The method of claim 1 wherein the disease is diabetes, one of the chemicals is an enzyme which is aldose reductase and the chemical compound is glucose.

3. The method of claim 1 wherein the cells are retinal pigment epithelium cells.

4. The method of claim 1 wherein the cells are removed from a human patient, animal model or cell culture model.

5. The method of claim 4 wherein the cells are from the human patient who has diabetes.

6. The method of claim 1 wherein the method is used to test multiple concentrations of the chemical compound in a series of tests for the effectiveness.

7. The method of claim 1 wherein the scanning accounts for at least 90% by weight of the separated products produced in step (e).

8. The method of claim 1 wherein the results are automatically produced by a computer which determines an amount of the products produced in step (e) based upon area of at least some of the peaks and provides a visually readable report of the amount based upon the area.

9. The method of claim 8 wherein the report is a graph.

10. The method of claim 1 wherein the culture medium contains glucose as the chemical and wherein at least sorbitol and myo-inositol are measured as the products.

11. The method of claim 1 wherein the light absorbance is at 195 nm.

12. A method for quantitatively testing a chemical compound in vitro for effectiveness in altering enzyme activity of at least one enzyme involved in diabetes by measuring multiple enzymatic products present in the cells which comprises:

(a) treating mammalian cells in a culture medium in vitro with the chemical compound to be tested;
   (b) separating the treated cells from the culture medium;
   (c) disrupting the cells in a fluid medium producing an admixture consisting of cellular debris as a solid phase, and a liquid phase which contains the multiple enzymatic products;
   (d) removing the debris from the liquid phase;
   (e) subjecting the liquid phase to capillary electrophoresis in a single run wherein the multiple enzymatic products produced by the enzyme are separated;
   (f) continuously scanning the multiple enzymatic products separated in step (e) by the capillary electrophoresis with a spectrophotometer which measures light absorbance to produce a chart with peaks of light absorbance for each of the multiple enzymatic products; and
   (g) calculating areas of the peaks to determine a quantity of each of the multiple enzymatic products; and
   (h) determining the effectiveness of the compound in altering the enzyme activity by comparing the peaks of the multiple enzymatic products to the peaks produced from a control consisting of cells not treated with the compound.

13. The method of claim 12 wherein the cells are retinal pigment epithelium cells.

14. The method of claim 12 wherein the cells are removed from a human patient, animal model or cell culture model.

15. The method of claim 14 wherein the cells are from the human patient who has diabetes.

16. The method of claim 12 wherein the method is used to test multiple concentrations of the chemical compound in a series of tests for the effectiveness.

17. The method of claim 12 wherein the scanning accounts for at least 90% by weight of the treated enzyme products produced in step (e).

18. The method of claim 12 wherein the results are automatically produced by a computer which determines an amount of the products produced in step (e) based upon the area and provides a visually readable report of the amount based upon the area.

19. The method of claim 18 wherein the report is a graph.

20. The method of claim 12 wherein the culture medium contains glucose as the chemical compound and wherein at least sorbitol and myo-inositol are measured as the products.

21. The method of claim 12 wherein the light absorbance is at 195 nm.

22. A method for quantitatively testing a chemical compound in vitro for effectiveness in altering enzyme activity of at least one enzyme involved in diabetes by measuring multiple enzymatic products in cells from a diabetic patient which comprises:

(a) treating cells from a patient who has diabetes in a culture medium in vitro with the chemical compound to be tested;
   (b) separating the treated cells from the culture medium;
   (c) disrupting the cells in a fluid medium producing an admixture consisting of cellular debris as a solid phase, and a liquid phase which contains the multiple enzymatic products;
   (d) removing the debris from the liquid phase;
   (e) subjecting the liquid phase to capillary electrophoresis in a single run wherein the products produced by treating the cells with the compound are separated;
   (f) continuously scanning the multiple enzymatic products separated in step (e) by the capillary electrophoresis with a spectrophotometer which measures light absorbance to produce a chart with peaks of light absorbance for each of the multiple enzymatic products;

(g) calculating areas of the peaks to determine a quantity for each of the multiple enzymatic products; and (h) determining the effectiveness of the compound in altering the enzyme activity by comparing the peaks of the multiple enzymatic products to the peaks produced from a control consisting of cells not treated with the compound.

23. The method of claim 22 wherein the cells are retinal pigment epithelium cells.

24. The method of claim 22 wherein the method is used to test multiple concentrations of the chemical compound in a series of tests for the effectiveness.

25. The method of claim 22 wherein the scanning accounts for at least 90% by weight of the separated chemicals produced in step (e).

26. The method of claim 22 wherein the results are automatically produced by a computer which determines an amount of at least some of the separated chemicals produced in step (e) based upon the area and provides a visually readable report of the amount based upon the area.

27. The method of claim 22 wherein the visually readable report is a graph.

28. The method of claim 22 wherein the culture medium contains glucose as the chemical compound and wherein at least sorbitol and myo-inositol are measured as the products.

29. The method of claim 22 wherein the light absorbance is at 195 nm.

* * * * *